(12) United States Patent
Silber

(10) Patent No.: US 8,788,013 B2
(45) Date of Patent: Jul. 22, 2014

(54) METHOD OF ASSESSING VASCULAR REACTIVITY USING MAGNETIC RESONANCE IMAGING, APPLICATIONS PROGRAM AND MEDIA EMBODYING SAME

(75) Inventor: Harry A. Silber, Owings Mills, MD (US)

(73) Assignee: The Johns Hopkins University, Baltimore, MD (US)

( * ) Notice: Subject to any disclaimer, the term of this patent is extended or adjusted under 35 U.S.C. 154(b) by 1473 days.

(21) Appl. No.: 11/795,784

(22) PCT Filed: Jan. 19, 2006

(86) PCT No.: PCT/US2006/002261
§ 371 (c)(1),
(2), (4) Date: May 16, 2008

(87) PCT Pub. No.: WO2006/079018
PCT Pub. Date: Jul. 27, 2006

(65) Prior Publication Data
US 2009/0093703 A1 Apr. 9, 2009

Related U.S. Application Data

(60) Provisional application No. 60/645,499, filed on Jan. 19, 2005.

(51) Int. Cl.
*A61B 5/05* (2006.01)

(52) U.S. Cl.
USPC ........... 600/410; 600/419; 382/128; 382/130; 382/131

(58) Field of Classification Search
USPC ........... 600/407, 411, 419; 382/128, 130, 131
See application file for complete search history.

(56) References Cited

U.S. PATENT DOCUMENTS 6,654,628 B1 * 11/2003 Silber et al. .................. 600/410
6,702,744 B2  3/2004 Mandrusov et al.

\* cited by examiner

*Primary Examiner* — Baisakhi Roy
(74) *Attorney, Agent, or Firm* — Johns Hopkins Technology Transfer

(57) ABSTRACT

Featured are methods for non-invasive assessment of vascular reactivity. The methods of the invention use phase contrast magnetic resonance imaging angiography and use the image data thereby acquired to measure shear rate, radius of the vasculature and flow through the vasculature. According to one aspect, such acquisition of image data occurs before and during, an arterial occlusion and according to another aspect such acquisition of image data occurs before during and after arterial occlusion. The disclosed methods of the invention allow for reproducible, non-invasive diagnosis of early stage indicators of atherosclerosis.

20 Claims, 17 Drawing Sheets

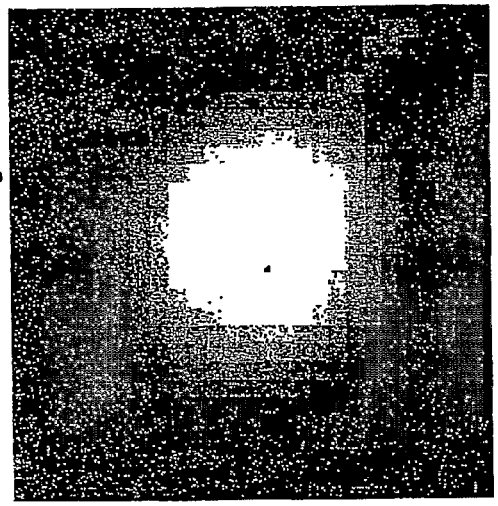
FIG. 11C
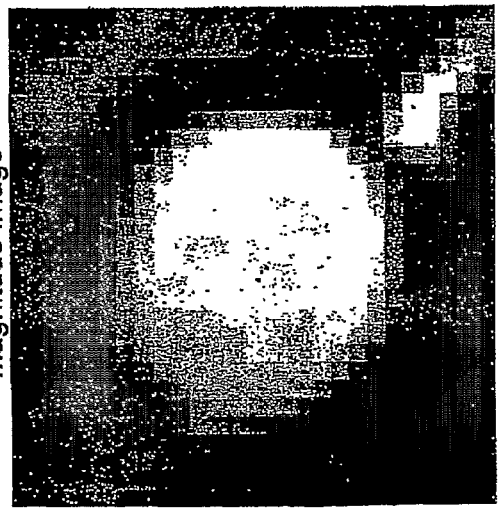
FIG. 11A
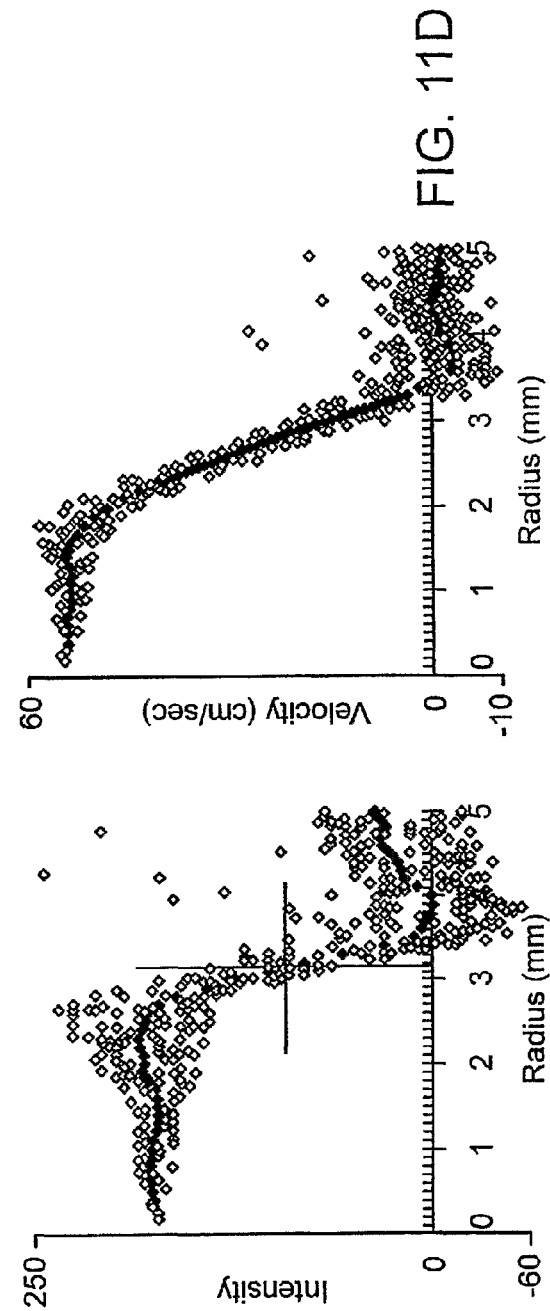
FIG. 11D
FIG. 11B

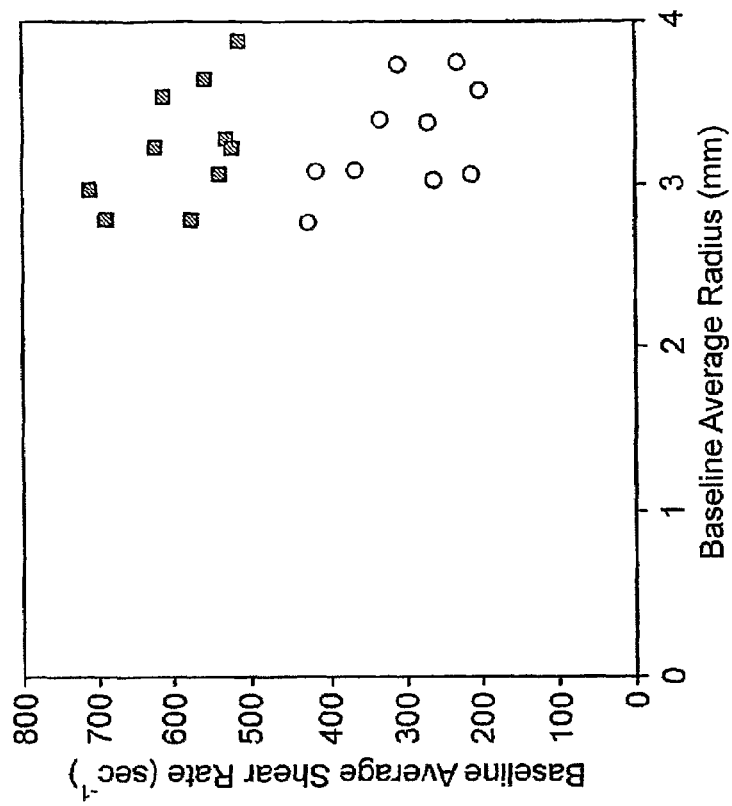
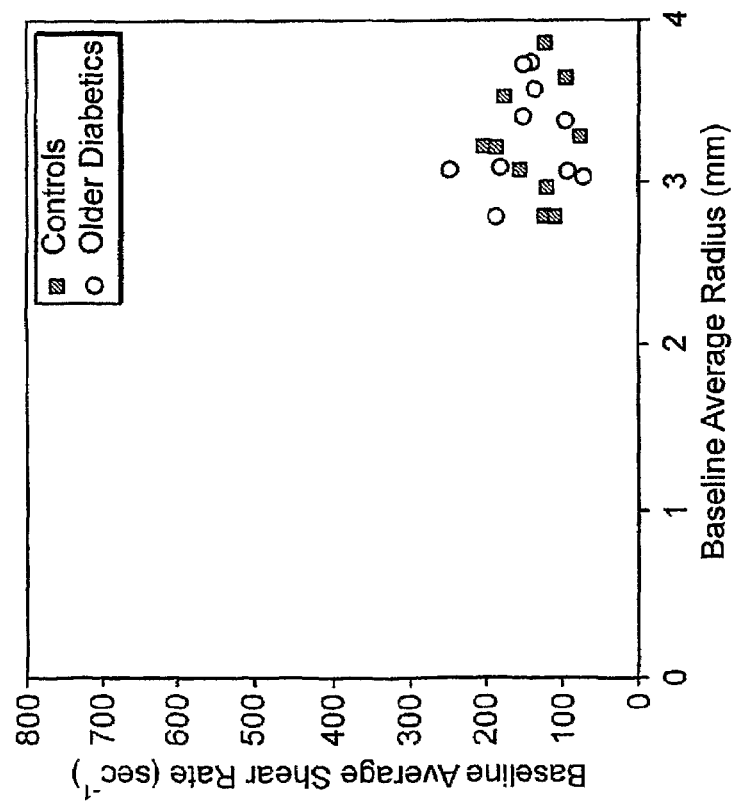
FIG. 13A
FIG. 13B

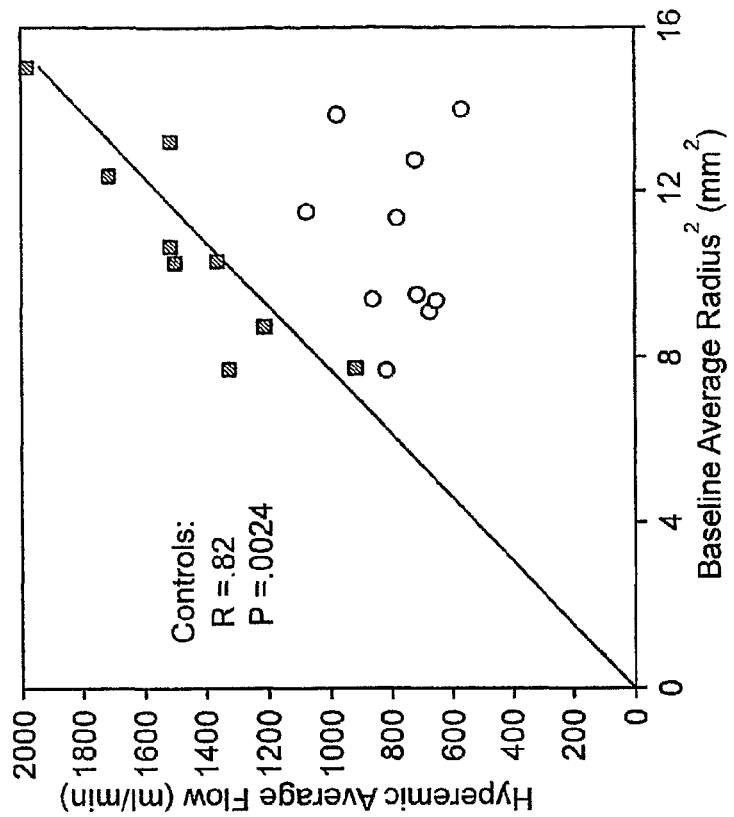
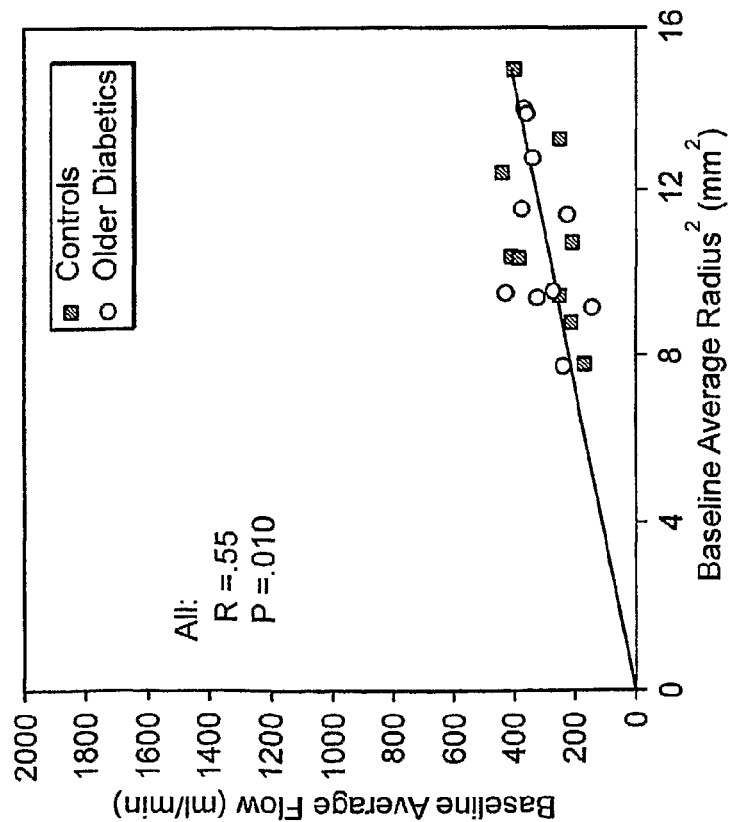
FIG. 14B
FIG. 14A

METHOD OF ASSESSING VASCULAR REACTIVITY USING MAGNETIC RESONANCE IMAGING, APPLICATIONS PROGRAM AND MEDIA EMBODYING SAME

STATEMENT REGARDING FEDERALLY-SPONSORED RESEARCH

This invention was made with government support under grant number HL004477 awarded by the National Institutes of Health. The government has certain rights in the invention.

CROSS-REFERENCE TO RELATED APPLICATIONS

This application is a 35 U.S.C. §371 U.S. national entry of International Application PCT/US06/02261, having an international filing date of Jan. 19, 2006, which claims the benefit of U.S. Provisional Application No. 60/645,499, filed Jan. 19, 2005, the content of each of the aforementioned applications is herein incorporated by reference in their entirety.

FIELD OF INVENTION

The present invention relates to the field of non-invasive assessment of vascular reactivity and more particularly to methods using phase contrast magnetic imaging angiography to measure wall shear rate and radius of vasculature of a patient that is being imaged.

BACKGROUND OF THE INVENTION

Vascular endothelium, the inner lining of blood vessels, is crucially important to maintaining vascular health. Endothelial cells regulate thrombosis, inflammation, vasomotion, and cell proliferation through the synthesis and release of substances including nitric oxide and endothelin-1. Cardiovascular risk factors are associated with endothelial dysfunction, and agents that reduce cardiovascular risk also improve endothelial function. Hence, endothelial dysfunction is considered to be an important common pathway by which risk factors promote atherosclerosis. Furthermore, endothelial dysfunction is associated with coronary events. Consequently, there is much interest in assessing endothelial function noninvasively.

Vascular endothelial dysfunction also has been found to be the earliest detectable occurrence in the development of atherosclerosis. Function of the vascular endothelium is affected by various factors including the presence of various substances such as oxidized low-density lipoprotein and nitric oxide, or by physical stimuli. Therefore, assessment of vascular physiology is important in detecting and tracking the development of early stage atherosclerosis. Additionally, it will also be crucial to studies in inflammation, stroke, hypertension and diabetes research, as well as additional complications affected by atherosclerosis.

Arterial smooth muscle relaxation is mediated by endothelial dependent mechanisms (Furchgott R F, Zawadski J V. The obligatory role of endothelial cells in the relaxation of arterial smooth muscle by acetylcholine. *Nature*. 1980; 288: 373.), which involve the release of nitric oxide (Palmer R, et al. Nitric oxide release accounts for the biologic activity of endothelium-derived relaxing factor. *Nature*. 1987; 327:524-526.). In vitro, the primary hemodynamic determinant of endothelial release of nitric oxide and subsequent vasodilation is wall shear stress (WSS) (Koller A, Kaley G. Endothelial regulation of wall shear stress and blood flow in skeletal muscle microcirculation. *Am J Physiol.* 1991; 260:H862-H868.; Koller A, et al. Role of shear stress and endothelial prostaglandins in flow- and viscosity-induced dilation of arterioles in vitro. *Circ Res* 1993; 72:1276-1284.; Busse R, et al. Signal transduction in endothelium-dependent vasodilation. *Eur Heart J.* 1993; 14:Suppl I, 2-9.; Busse R, Fleming I. Pulsatile stretch and shear stress: physical stimuli determining the production of endothelium-derived relaxing factors. *Journal of Vascular Research.* 1998; 35:73-84.) Larger increases in non-pulsatile shear stress have been shown to produce greater increases in diameter of isolated arteries from rat skeletal muscle (Koller A, Kaley G. Endothelial regulation of wall shear stress and blood flow in skeletal muscle microcirculation. *Am J Physiol.* 1991; 260:H862-H868.). However, the effects of pulsatile shear stress are different than those of constant shear stress (Ziegler T, et al. Influence of oscillatory and unidirectional flow environments on the expression of endothelin and nitric oxide synthase in cultured endothelial cells. *Arterioscler Thromb Vasc Biol.* 1998; 18:686-692.; Malek A M, et al. Modulation by pathophysiological stimuli of the shear stress-induced up-regulation of endothelial nitric oxide expression in endothelial cells. *Neurosurgery.* 1999; 45:334-344.).

In humans, reduced flow-mediated dilation (FMD) in hypertension has been found to result from at least in part lower baseline systolic wall shear stress (WSS) (Khder Y, et al. Shear stress abnormalities contribute to endothelial dysfunction in hypertension but not in type II diabetes. *J Hypertens.* 1998; 16:1619-1625.). Conversely, an increase in blood flow following a brief period of skeletal muscle ischemia is accompanied by dilation of the conduit artery (Sinoway Li et al. Characteristics of flow-mediated brachial artery vasodilation in human subjects. *Circ Res.* 1989; 64:32-42.; Celermajer D S, et al. Noninvasive detection of endothelial dysfunction in children and adults at risk of atherosclerosis. *Lancet.* 1992; 340: 1111.). Furthermore, increases in the magnitude or duration of hyperemia lead to increased vasodilation, while arterial diameter decreases during a low-flow state caused by distal arterial occlusion (Corretti M C, et al. Technical aspects of evaluating brachial artery vasodilation using high-frequency ultrasound. *Am J Physiol.* 1995; 268:H1397-H1404.; Leeson P, et al. Non-invasive measurement of endothelial function: effect on brachial artery dilation of graded endothelial dependent and independent stimuli. *Heart.* 1997; 78:22-27.). The relationship between WSS and arterial flow-mediated dilation (FMD) in humans was previously established (Silber H S, et al, The Relationship Between Vascular Wall Shear Stress and Flow-Mediated Dilation: Endothelial Function Assessed by Phase-Contrast Magnetic Resonance Angiography, JACC 2001; Vol. 38, No. 7; December 2001: 1859-65).

Vascular physiology can be assessed, in part, through measurements of endothelial function. Changes in the diameter of an artery in response to a stimulus such as change in blood flow velocity through the artery (arterial wall shear stress, WSS) are indicative of endothelial function, known as flow mediated dilation (FMD). Endothelial function can be measured by inflating a blood pressure cuff around a subject's arm and monitoring velocity of blood flowing through a brachial artery while measuring the artery's diameter before, during and after the inflation of the cuff.

Ultrasound measurements of flow mediated dilation have been widely used to study endothelial function in patients with known cardiac risk factors with (Hoeks A P G, et al. Noninvasive determination of shear-rate distribution across the arterial lumen. *Hypertension.* 1995; 26:26-33.; Levine G N, et al. Ascorbic acid reverses endothelial vasomotor dysfunction in patients with coronary artery disease. *Circulation.* 1996; 93:210-214.; Vogel R A, et al. Changes in flow-mediated brachial artery vasoreactivity with lowering of desirable cholesterol levels in healthy middle-aged men. *Am J. Cardiol.* 1996; 77:37-40.; Motoyama T, et al. Endothelium-dependent vasodilation in the brachial artery is impaired in smokers: effect of vitamin C. *Am J Physiol.* 1997; 273:H1644-H1650.; Plotnick G D, et al. Effect of antioxidant vitamins on the transient impairment of endothelial-dependent brachial artery vasoactivity following a single high-fat meal. *JAMA.* 1997; 278:1682-1686.; Hornig B, et al. Vitamin C improves endothelial function of conduit arteries in patients with chronic heart failure. *Circulation.* 1998; 97:363-368.; Neunteufl T, et al. Additional benefit of vitamin E supplementation to simvastatin therapy on vasoreactivity of the brachial artery of hypercholesterolemic men. *J Am Coll Cardiol.* 1998; 32:711-716.; Chambers J C, et al. Demonstration of rapid onset vascular endothelial dysfunction after hyperhomocysteinemia: an effect reversible with vitamin C therapy. *Circulation.* 1999; 99:1156-1160.) and without (Celermajer D S, et al. Noninvasive detection of endothelial dysfunction in children and adults at risk of atherosclerosis. *Lancet.* 1992; 340: 1111.; Celermajer D S, et al. Cigarette smoking is associated with dose-related and potentially reversible impairment of endothelium-dependent dilation in healthy young adults. *Circulation.* 1993; 88:2149-2155.; Celermajer D S, et al. Passive smoking and impaired endothelium-dependent arterial dilation in healthy young adults. *N Engl J Med.* 1996; 334:150-154.) intervention. However, there is considerable overlap in the arterial dilatory response between individuals with and without cardiac risk factors (Corretti M C, et al. Technical aspects of evaluating brachial artery vasodilation using high-frequency ultrasound. *Am J Physiol.* 1995; 268:H1397-H1404.; Celermajer D S, et al. Cigarette smoking is associated with dose-related and potentially reversible impairment of endothelium-dependent dilation in healthy young adults. *Circulation.* 1993; 88:2149-2155.; Celermajer D S, et al. Passive smoking and impaired endothelium-dependent arterial dilation in healthy young adults. *N Engl J Med.* 1996; 334:150-154.). This is in part because FMD is inversely related to baseline diameter (Celermajer D S, et al. Noninvasive detection of endothelial dysfunction in children and adults at risk of atherosclerosis. *Lancet.* 1992; 340:1111.). There is evidence from the study of rat skeletal muscle arterioles that this inverse relationship may be due to an inverse relationship between baseline diameter and wall shear stress (Koller A, Kaley G. Endothelial regulation of wall shear stress and blood flow in skeletal muscle microcirculation. *Am J Physiol.* 1991; 260:H862-H868.).

Current methods to assess endothelial function non-invasively use ultrasound to measure flow mediated dilation of a limb artery after release of a temporary occlusion of that limb. This method exploits the fact that shear stress is the primary hemodynamic stimulus of endothelial function, and that increased shear stress induces dilation in human peripheral arteries due primarily to nitric oxide release. However, use of ultrasound poses problems for assessment of vascular endothelial function. In addition to those technical problems discussed above wherein there is significant overlap of readings between patient populations, ultrasound measurements may be poorly reproducible because the technique is highly operator dependent with regard to probe positioning. Additionally, although dilation may be measured additional measurements to determine shear stress stimulus by ultrasound can only be accomplished using sophisticated, non-standard, signal processing equipment.

Conversely with hyperemia-induced dilation, decreased flow induces constriction of peripheral arteries. Low-flow mediated constriction is also endothelial-dependent, and is mediated by endothelin-1 via endothelin A receptors. However, low-flow mediated constriction has been studied much less extensively than flow mediated dilation. Furthermore, the relationship between the stimulus of shear reduction and the response of vasoconstriction has not been determined. In another method, phase contrast magnetic resonance imaging (PCMRI) is used to determine the relationship between flow mediated dilation and the hyperemic shear stimulus for flow mediated dilation.

It thus would be desirable to provide new non-invasive methods for assessing vasculature reactivity using magnetic resonance imaging as well as applications programs embodying such methods. It would be particularly desirable to provide such methods that would measure shear rate and/or vasculature dimensions. It also would be desirable to provide such methods in which such characteristics are measured during either of decreased or increased flow conditions as well as using techniques that user-independent.

The references discussed herein are provided solely for their disclosure prior to the filing date of the present application. Nothing herein is to be construed as an admission that the inventors are not entitled to antedate such disclosure by virtue of prior invention.

SUMMARY OF THE INVENTION

The present invention features methods for non-invasive assessment of vasculature reactivity using magnetic resonance imaging. In more particular aspects, such assessment is made when the flow through the vasculature is decreased from normal conditions such as by constricting the vasculature or when the flow through the vasculature is increased such as that which occurs after the mechanism constricting the vasculature is removed. In more particular embodiments, such methods include using phase contrast magnetic resonance imaging to obtain the image data of the vasculature being evaluated. Further such methods, include using the acquired image data to directly measure the shear rate, vasculature dimensions and/or flow through a cross-section of the vasculature, when the flow is decreased or increased as described herein. Also featured are applications programs for execution on a microprocessor or computing device to process the image data and so as to yield measurements of the shear rate and/or vasculature dimensions. Such application programs and methods further embody one or more algorithms to measure the vasculature dimensions and/or the shear rate.

Such methods are particularly advantageous as the methodology provides a mechanism by which people at risk for atherosclerosis development, even years before atherosclerosis develops in them, can be identified non-invasively. Such methods are beyond just screening patients at risk for atherosclerosis, the present invention provides the type of analysis and data for the development and use of anti-atherosclerotic primary preventive or secondary preventive therapy. Also, and as indicated herein, the applications program(s) or the software package of an MRI scanner for new MRI scanners can be adapted, or the program could be sold to end-users as a software upgrade for existing MRI scanners either currently with or without cardiovascular software.

The present invention also advantageously can measure shear rate directly, efficiently, precisely, and with an automated, user-independent algorithm. Moreover, shear rate can be measured during transient hyperemia or during low-flow, which are both endothelial-dependent processes, and which are both stimuli for vasoactivity. Furthermore, a computationally efficient and precise algorithm is used to measure arterial dimension. Also, the MRI-based algorithm is used to measure low-flow mediated constriction. Overall, the present invention enhances the assessment of vascular endothelial function.

As indicated herein, according to one aspect of the present invention, there is featured a methodology for assessing vascular reactivity including measuring shear rate, vasculature dimension and/or flow of fluid in the vasculature at a time when vasculature is being occluded. Such a method includes:

(a) using a magnetic resonance imaging scanner to obtain images;

(b) locating an artery using coronal scout images;

(c) positioning the subject or patient, such that the artery is parallel to a magnet bore of the magnetic resonance imaging scanner and cross sectional images can be thus obtained;

(d) constricting the artery for a time period, whereby the artery is fully occluded;

(e) acquiring images of the artery prior to occlusion (at baseline), as well as one or more times during occlusion;

(f) using the acquired image data and measuring the shear rate and/or radius of the artery at baseline and for each of the one or more times during occlusion; and (g) determining from the measured values if the values are outside the range of normal individuals, whereby a outside the range is indicative of abnormal vascular endothelial function.

In further embodiments, such a methodology further includes arranging the image data so as to be in N sectors, where N is an integer and where N≥2. In an illustrative exemplary embodiment N≥12. Performing said step of using the acquired image data and measuring the shear rate and/or radius of the artery at baseline and for each of the one or more times during occlusion for each of the N sectors such that there are N measured values.

As indicated herein, according to another aspect of the present invention, there is featured a methodology for assessing vascular reactivity including measuring shear rate, vasculature dimension and/or flow of fluid in the vasculature at a time principally after the vasculature is being occluded. Such a method includes:

(a) using a magnetic resonance imaging scanner to obtain images;

(b) locating an artery using coronal scout images;

(c) positioning the subject or patient, such that the artery is parallel to a magnet bore of the magnetic resonance imaging scanner and cross sectional images can be thus obtained;

(d) constricting the artery for a time period, whereby the artery is fully occluded;

(e) releasing the artery from occlusion;

(f) acquiring images of the artery prior to occlusion (at baseline), as well as during occlusion, and at time periods following release from occlusion;

(g) using the acquired image data and measuring the shear rate and/or radius of the artery at baseline and for each of the one or more times during occlusion; and (h) determining from the measured values if the values are outside the range of normal individuals, whereby a outside the range is indicative of abnormal vascular endothelial function.

In further embodiments, such a methodology further includes arranging the image data so as to be in N sectors, where N is an integer and where N≥2. In an illustrative exemplary embodiment N≥12. Performing said step of using the acquired image data and measuring the shear rate and/or radius of the artery at baseline and for each of the one or more times during occlusion for each of the N sectors such that there are N measured values.

As indicated herein the present invention also features an application or software program for execution on a computer, computing device or microprocessor as is known to those skilled in the art. Such software or applications program includes code segments, instruction and criteria to acquire the image data, to process the image data so as to measure the shear rate, the radius of the artery and/or the flow through the artery as embodied in and described herein for any of the methodologies of the present invention. Also featured is a computer readable medium on which is stored such an applications program or software.

In further embodiments, there is featured a data processing system including a computer, computing device or microprocessor as is known to those skilled in the art and an applications program or software as herein described, which is loaded onto the computer, computing device or microprocessor for execution therein.

Other aspects and embodiments of the invention are discussed below.

DEFINITIONS

The instant invention is most clearly understood with reference to the following definitions:

A computer readable medium shall be understood to mean any article of manufacture that contains data that can be read by a computer or a carrier wave signal carrying data that can be read by a computer. Such computer readable media includes but is not limited to magnetic media, such as a floppy disk, a flexible disk, a hard disk, reel-to-reel tape, cartridge tape, cassette tape or cards; optical media such as CD-ROM and writeable compact disc; magneto-optical media in disc, tape or card form; paper media, such as punched cards and paper tape; or on carrier wave signal received through a network, wireless network or modem, including radio-frequency signals and infrared signals.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 11A is a baseline magnitude image at peak systole for a typical subject;

FIG. 11B is a graphical radial plot of magnitude pixel data, smoothed average and full width-half maximum;

FIG. 11C is a baseline phase image at peak systole;

FIG. 11D is a graphical radial plot of phase pixel data, smoothed average and best-fit parabola segment;

FIG. 13A is a graphical plot of baseline average shear rate versus baseline average radius;

FIG. 13B is a graphical plot of hyperemic average shear rate versus baseline average radius;

FIG. 14A is a graphical plot of baseline average flow versus baseline average radius;

FIG. 14B is a graphical plot of hyperemic average flow versus baseline average radius;

FIG. 17A is during peak systole and FIG. 17C is during peak negative flow.

DESCRIPTION OF THE PREFERRED EMBODIMENT

Figure 1:
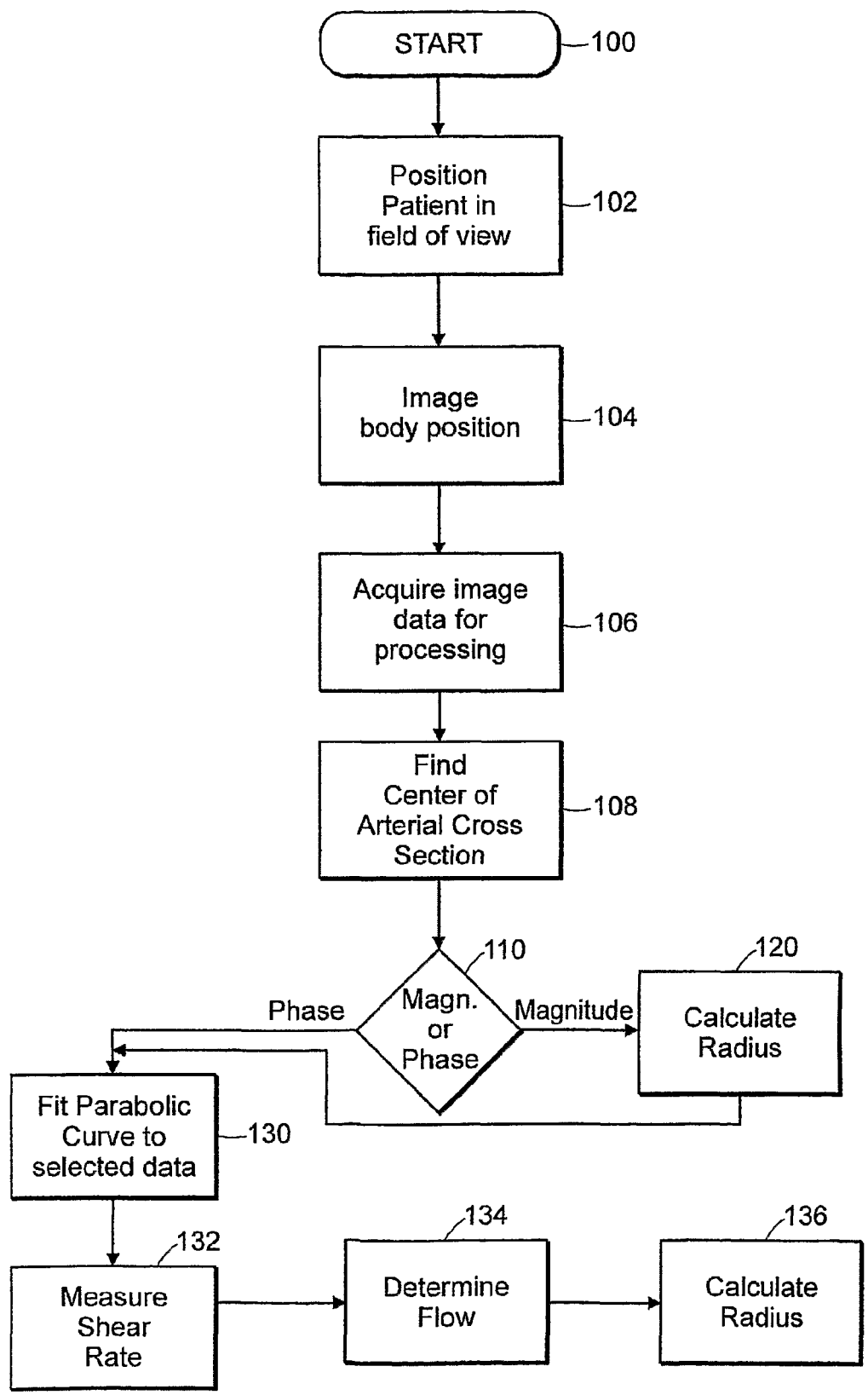
FIG. 1 is a high level flow diagram of the methodology of the present invention for measuring shear rate and/or radius.

The present invention features various methods that can assess vascular endothelial function using phase contrast magnetic resonance angiography. More particularly, such methods provide for measuring directly the shear stress rate and radius of the vasculature being imaged as well as allowing the clinician to assess vascular endothelial function and resulting arterial dilation or constriction in humans. More specifically, with the present invention, the shear rate is measured directly, efficiently, precisely, and with an automated, user-independent algorithm. Furthermore, a computationally efficient and precise algorithm is used to measure arterial dimension. Also, the MRI-based algorithm is usable to measure low-flow mediated constriction. Overall, the methods of the present invention enhance the assessment of vascular endothelial function.

Phase contrast magnetic resonance angiography (PC-MRA) allows for images which can provide cross sectional area and spatially blood flow velocity readings simultaneously; thus, it readily allows for the measurement of vascular wall shear rate as well as simultaneous measuring the radius of the vasculature when dilated or contracted. A fixed cross section can be imaged repeatedly, thus reducing operator dependence.

As discussed herein, the methods of the present invention allow for assessing vascular endothelial function using phase contrast magnetic resonance angiography (PCMRA). In general and according to one aspect of the present invention, such methods comprise or consist of the following:

a person lies in scanner with a receiver coil and a sphygmomanometer, or inflatable cuff (e.g., inflatable blood pressure cuff) on the limb;

phase contrast magnetic resonance images are obtained of the arterial cross section at baseline;

the cuff is inflated to a pressure above the maximum systolic pressure of the person in order to block the artery completely, for a period of about five minutes; and phase contrast magnetic resonance images are obtained of the arterial cross section at time intervals while the artery is blocked.

As discussed herein, the methods of the present invention allow for assessing vascular endothelial function using phase contrast magnetic resonance angiography (PCMRA). In general and according to another aspect of the present invention, such methods comprise or consist of the following:

a person lies in scanner with a receiver coil and a sphygmomanometer, or inflatable cuff (e.g., inflatable blood pressure cuff) on the limb;

phase contrast magnetic resonance images are obtained of the arterial cross section at baseline;

the cuff is inflated to a pressure above the maximum systolic pressure of the person in order to block the artery completely, for a period of about five minutes, the pressure is released; and phase contrast magnetic resonance images are obtained of the arterial cross section at intervals following release of occlusion.

Scanning images may be taken at any intervals from immediately post release of occlusion of the artery through any stage of recovery, including two, five, or ten minutes post release. For example, PCMRA images are obtained of the arterial cross section at about 1 minute to about 5 minutes after cuff release has occurred. Additionally, PCMRA images are obtained during peak reactive hyperemia, within about 20-30 seconds to about 1 minute after cuff release.

Referring to FIG. 1, there is shown a high level flow diagram of a user-independent algorithm according to the present invention that is usable to determine radius of an arterial cross section from the magnitude image or phase image of a phase-contrast MRI scan and also to determine the shear rate and flow velocity of an arterial cross-section from the phase image of a phase-contrast MRI scan. It is within the scope and skill of those knowledgeably in the art to adapt the below described algorithm so as to be used with pixel arrays of different sizes and arrangements as well as subset arrays of different arrangements and configurations than that described below.

The methodology is started, Step 100 at the time a patient is to be imaged using an MRI technique to acquire the image data for processing in accordance with the present invention. Such starting includes preparing the MRI devices and apparatus that are to be used to carryout the imaging. Such MRI devices and apparatus are well known in the art.

Before acquiring the image data that is to be processed as described herein, the patient is arranged or positioned so that the region or area of interest, more specifically the vasculature cross-section to be imaged, will be located or positioned in the center of the image, Step 100. It should be recognized that while it is desirous to position the cross-section of the vasculature to be imaged so it would be generally located or positioned in the center of the image, it is within those skilled in the art to adapt the below described procedure so that it can process an image where the cross-section of the vasculature to be imaged would not be located or positioned in the center in the image. Typically, and as described below in the examples, one images the object or patient before acquiring the image data to be processed so as to position the object/person for data acquisition.

After the patient or object is positioned, the clinician or technician images the body portion, Step 104. After the image data is obtained, the imaged data is acquired (i.e., imported into the computer) for processing, Step 106. More particularly, a pixel array of a magnitude image or the phase image (for example a 256 by 256 pixel array) is acquired for processing. It should be recognized that the pixel array can form any of a number of numerical arrays as is known to those skilled in the art.

After acquiring the pixel array, and using the magnitude or phase image the center of the arterial cross-section is determined, Step 108. In a particular illustrative embodiment the center of the arterial cross section is determined using the following steps.

1. Take a subset (e.g., a 40×40 subset) from the center of the pixel array.
2. Consider a box of pixels (e.g., a 5×5 box of pixels) inside the subset array and move that box around the array.
3. Locate the center of the box array position with the highest average intensity.
4. Use the value of the average intensity of that box as the maximum intensity inside the arterial cross-section.
5. Average the pixels in the areas surrounding the largest possible arterial cross-section and use that value as the background or zero intensity.
6. Calculate intensity range (i.e., intensity range=#6 minus #7).
7. Choose a plateau level, from 10% to 150% of the intensity range
8. Make a new subset array (e.g., a 40×40 array) called "Top" and for each pixel in the original subset array, if the pixel intensity is greater than the plateau value, set the corresponding pixel in the Top array equal to the plateau value. Otherwise, set the pixel equal to that of the original subset array. This has the effect of chopping off the top of the magnitude profile.
9. Make a new subset array (e.g., a 40×40 array) called "Plateau" and for each pixel, if the corresponding pixel and any other pixel adjacent to it in Top are equal to the plateau value, set that pixel to 1. Otherwise, set that pixel equal to 0. Set the outer 1-pixel frame of pixels equal to 0.
10. Make a new subset array (e.g., a 40×40 array) called "Mass" and for each pixel in Mass, if the corresponding pixel in Plateau equals 1, add one to the contiguous pixels in Plateau that equal 1, up to five pixels away in any orthogonal direction. Make that sum the value of the pixel in Mass. Set the outer 5-pixel-wide frame of pixels to 0.
11. Find the maximum pixel value in the Mass array. Maximum possible value equals 21.
12. Make a new subset array (e.g., a 40×40 array) called "Peak." For each pixel, if its value in Mass equals the maximum pixel value in Mass, set the pixel equal to 1. Otherwise, set it equal to 0.
13. Find the geometric center of the Peak array.
14. Make a radial plot of the original data minus the calculated background level, using that geometric center as the center.
15. Make a smoothed average of the radial plot.
16. Calculate the dispersion of points by taking a sum of squares of the distance between each point and the smoothed average.
17. Repeat steps 7-16 for each plateau level.
18. Choose the plateau level that resulted in the lowest dispersion, i.e. the least sum of squares. Use the coordinates of the center that resulted from using the chosen plateau level.
19. Move the center one-half pixel in each orthogonal direction or in both orthogonal axes. There will then be nine possible center locations.
20. For each of the nine possible positions of the new center, calculate the dispersion of points around the smoothed average using the sum of squares method.
21. Choose the adjusted center that resulted in the least sum of squares.

Thereafter, the process proceeds based on whether the image used in determining the center of the arterial cross-section is the magnitude image or the phase image, Step 110. If the magnitude image was used to find the center (Step 110, magnitude), then the radius of the arterial cross-section is calculated or determined, Step 120. In an illustrative exemplary embodiment, the radius is calculated by calculating the distance from the adjusted center to where the intensity drops to half its maximum value. Thereafter, the process proceeds to Step 130.

If the phase image data was used to find the center (Step 110, phase) or after calculating the radius in Step 120), then the process proceeds to fit a parabolic curve to the velocity data of the phase image, Step 130. In a particular illustrative embodiment the fitting of the parabolic curve to the velocity data is obtained using the following steps.

A. Make a larger subset array (e.g., an 80×80 subset array) from the center of the original pixel array of the phase image.

B. Average the pixels in the areas surrounding the largest possible arterial cross-section and use that value as the background or zero velocity.

C. Take a 40×40 subset from the center of the 256×256 array of the phase image.

D. Using the adjusted center calculated from steps 1-23, make a radial plot of the phase data minus the background.

E. Find the maximum velocity of the phase data.

F. Find the radius where the velocity drops below a preset percentage of the maximum velocity. In particular embodiments, the preset percentage of the maximum velocity is in the range of from about 5 to 20% and in an exemplary embodiments is about 15%

Figure 2:
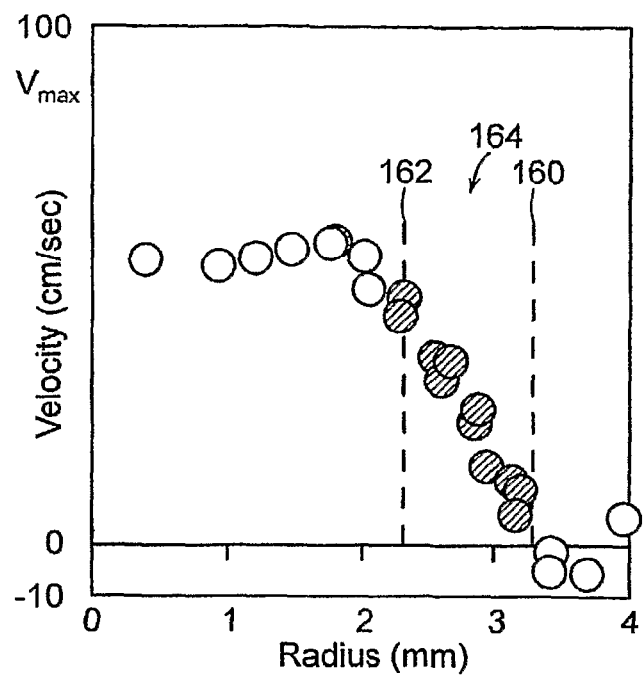
FIG. 2 is an illustrative graphical figure of velocity versus radius showing the radial segment for best fitting a parabola.

G. Using that radius or first point 160 (FIG. 2) as the outer limit, identify a radial segment 164 that is between that first point and a second point 162 that is located a preset distance inward toward the center. In particular embodiments, the preset distance is in the range of between about 10 to 50% of the radius from Step F, more particularly the preset distance is between about 0.5 to 2 mm, and yet more particularly the preset distance is about 1 mm.

Figure 3:
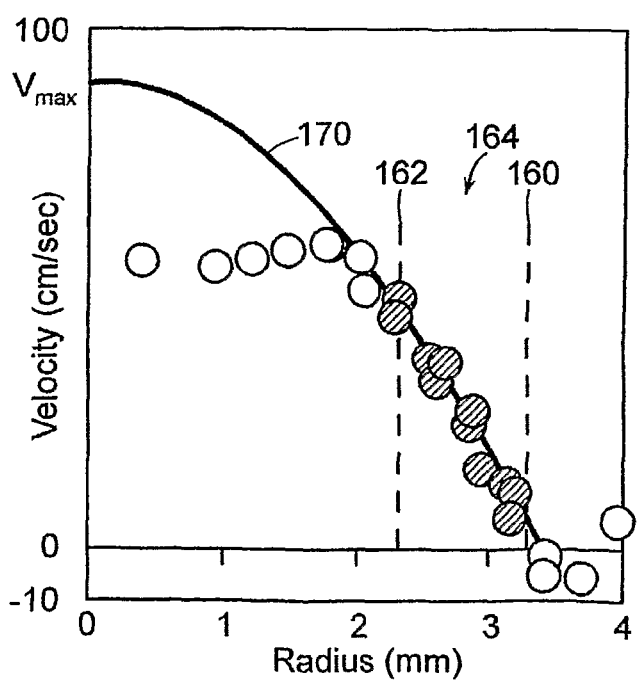
FIG. 3 is an illustrative graphical figure of velocity versus radius showing a parabolic curve fitted to the velocity data.
Figure 4:
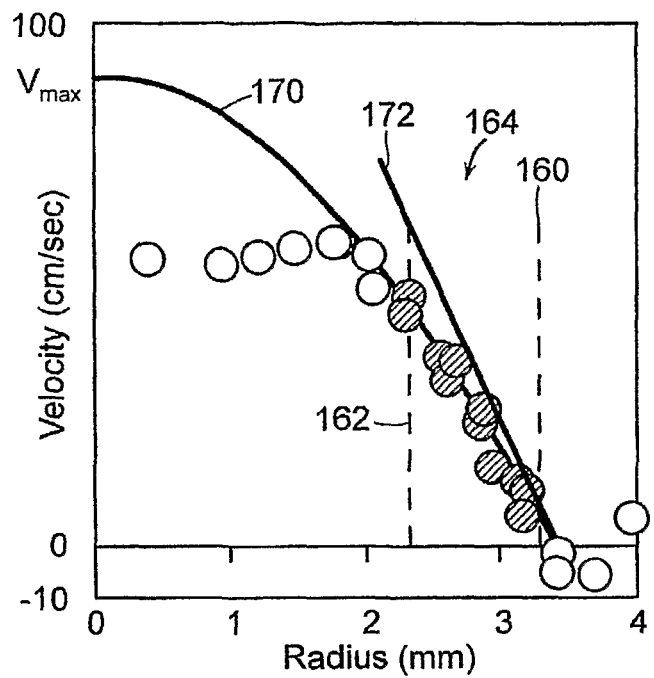
FIG. 4 is an illustrative graphical figure of velocity versus radius showing the slope of the parabolic curve corresponding to the shear rate.

H. Find the equation of a parabola 170 (FIG. 3) that best fits (by sum of squares analysis) the velocity data in that segment. In particular embodiments, the velocity data in that segment is the velocity data as a function of radius for each of N sections of the phase image. Thus, the equation of the parabola is fitted to all the velocity data of the N sections and not just one section at a time. N is an integer ≥2 and in more particular embodiments is an integer in the range of from about 4 to 128 and yet in more particular embodiments N is 12.

Figure 5:
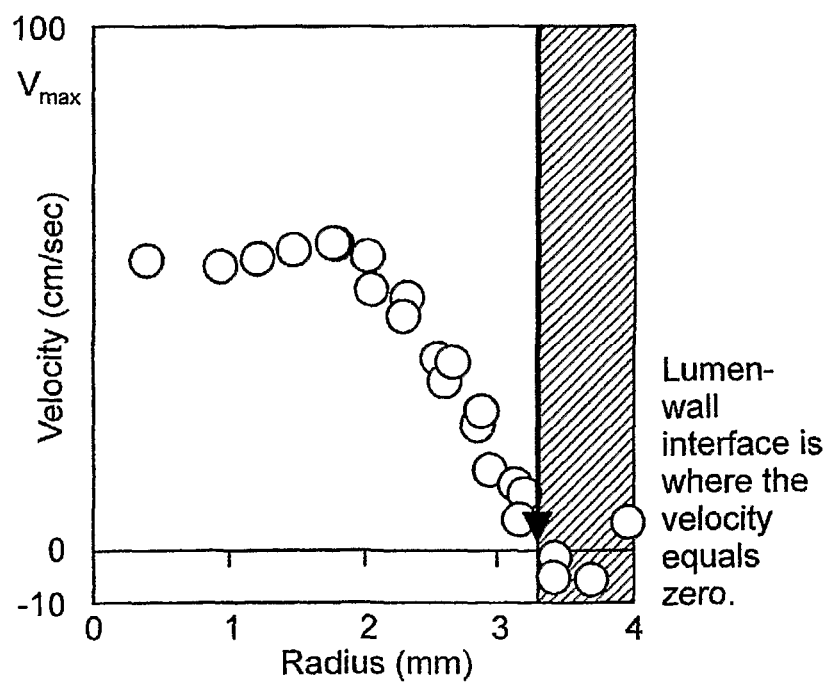
FIG. 5 is an illustrative graphical figure of velocity versus radius showing the lumen-wall interface.

I. Using the equation of the best-fit parabola, calculate the slope at where the velocity would equal zero. This is the shear rate of the artery. The radius at which the velocity would equal zero is the radius of the artery (FIG. 5).

Thereafter, the flow is determined, Step 134. In a particular illustrative embodiment the flow is determined by summing the velocity pixels whose distance from the center is less than the radius where the velocity drops below the preset value or percentage of maximum. This is the flow in the artery.

In the case, where the center of the arterial cross-section was determined using the phase image (Step 110, phase), the radius of the arterial cross-section is determined, Step 136. In an exemplary illustrative embodiment the radius is calculated using the equation of the parabola fitted to the velocity data in Step H. As indicated herein the velocity is zero at the lumen-wall interface (FIG. 5).

Alternatively, shear rate and/or radius can be determined using the following methodology in which image data also is imported into the microprocessor or computer for processing, such as for example imported into a spreadsheet-based program. The cardiac phase closest to peak systole was identified by choosing the image with the greatest peak velocity and was used for further analysis. In our approach, the limits of the arterial diameter were estimated in two orthogonal axes. An initial estimate of the center of the cross-section was calculated from those limits.

The cross-section was divided into 12 sectors around the estimated center. For each sector, outer radius of the velocity profile was estimated. A ring segment of datapoints with radius ranging from slightly less than the initially estimated outer radius to about 1 mm inward toward the estimated center was used. The velocity pixels in the ring segment of the sector were fit by least-squares method to a parabola with the assumption that blood flow velocity at the lumen wall is zero. Shear rate was calculated or measured as the slope of the velocity profile at the lumen-wall interface. Radius was calculated as the distance from the center of the velocity parabola to the point where the parabola crosses zero velocity.

The calculated lumen radius and shear values were averaged over the 12 sectors in the arterial cross-section. This approach provides sub-pixel precision in calculating lumen radius, and was shown to be accurate when compared to glass tubes of known manufactured diameter. Furthermore, the approach is not constrained by the geometry of the lumen perimeter, i.e. the arterial cross-section does not have to be perfectly circular. Systolic flow was measured directly by summing all of the velocity pixels in the arterial cross-section. Shear rate immediately after cuff inflation was calculated using flow measured at two minutes into cuff inflation, and using radius measured at baseline, using the Poiseuille equation:

$$\text{shear rate}=4k(\text{flow})/((\pi)(\text{radius}^3))$$

The constant k is necessary because the velocity profile during systole is slightly blunted rather than being a fully developed parabola. Consequently the true shear rate is greater than what would be calculated using a fully developed parabolic velocity profile. Thus k describes how many times greater the shear rate is than would be predicted by a fully developed paraboloid given the same radius and flow. The value of k was determined for each subject by directly measuring radius, flow, and shear rate at baseline and at 2-minutes into cuff inflation. The value of the k was solved for:

$$k=((\pi)(\text{radius}^3))/(4(\text{flow})(\text{shear rate}))$$

The value of k at 2 minutes into cuff inflation was used in the calculation of shear rate immediately after cuff inflation. Degree of vasoconstriction was expressed as the percent change in radius from baseline to two minutes into cuff inflation.

Figure 6:
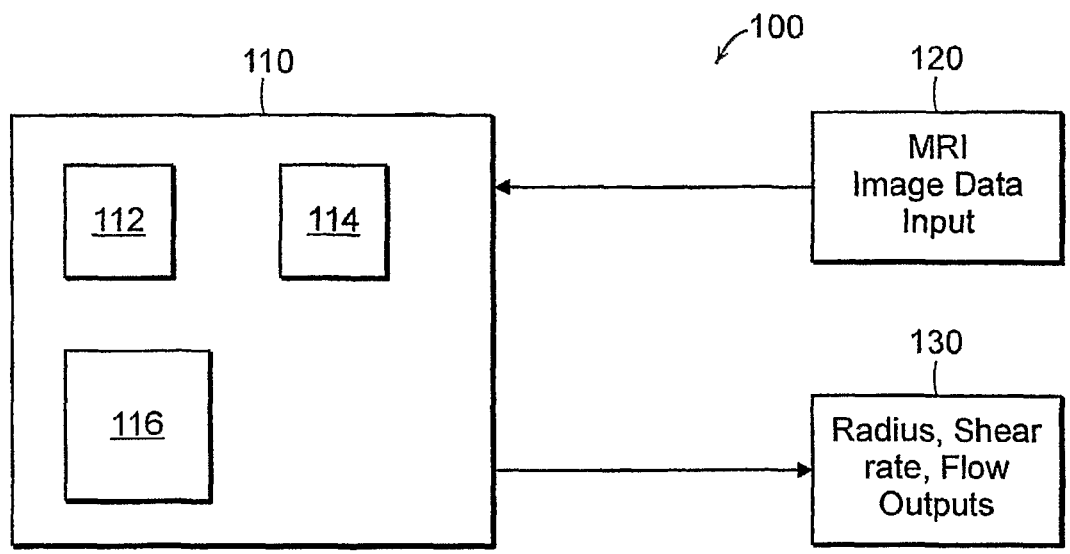
FIG. 6 is a schematic view of a computer system including an applications program embodying the methodology of the present invention for processing NM image data.

Referring now to FIG. 6 there is shown a schematic view of a computer system 200 for processing the image data and on which an applications program embodying the methodology described herein for measuring shear rate and radius is executed. Such a computer system 200 includes a computer 210 having a microprocessor 212, a memory 214 (e.g., RAM, NVRAM), and a storage device 216 on which programs such as the applications program embodying the methodology of the present invention and other information can be stored. The computer 210 receives MRI inputs 220 from MRI scanning or detection devices (e.g., coils). Such an applications program includes code segments, instructions and criteria for carrying out the methodology herein described. The computer 210 processes the MRI image data as herein described and provides outputs 230 of various parameters or characteristics of vascular reactivity such as shear rate, radius and flow.

Example 1

Subjects

Thirty-three healthy subjects (16 men and 17 women), ages 20-41, with no cardiovascular risk factors including hypertension, diabetes, hyperlipidemia, smoking, obesity or cardiac disease in a first-degree relative were studied. No subject was acutely ill or was on any vasoactive medication. The study protocol was approved by the Institutional Review Board at the Johns Hopkins School of Medicine. All subjects gave written informed consent.

Study Protocol

Subjects abstained from eating or drinking except water for at least 6 hours before the study. Baseline blood pressure was recorded. PCMRI was performed using a 1.5T scanner (CV/i, General Electric Medical Systems, Milwaukee, Wis.) equipped with cardiac gradient coils (40 mT/m, 120 T/m/s). Electrocardiographic leads were placed on the thorax. A dual cardiac phased array receiving coil was placed anterior and posterior to the upper thigh. A sphygmomanometer cuff was placed on the lower thigh. Phase-contrast images were obtained at baseline. The cuff was then inflated at least 20 mmHg above the subject's measured systolic blood pressure for 5 minutes. Images using the same fixed cross-sectional axial prescription as at baseline were obtained immediately after onset of cuff inflation and at two minutes into cuff inflation. Serum values of glucose, hematocrit, and fasting lipid panel were obtained after the scanning portion of the study. To assess the reproducibility of measurements, the study was repeated in each of eight subjects during a second session.

Imaging Protocol

Coronal and axial scout images were obtained to locate the superficial femoral artery and to verify that the artery was parallel to the magnet bore. Phase contrast scans were gated to the electrocardiogram signal. A single imaging plane perpendicular to the artery of interest was prescribed. The imaging parameters were: Matrix size 256×128, field-of-view 10 by 10 cm, slice thickness 3 mm, flip angle 25 degrees, bandwidth 31.2 kHz, repetition time (TR) 11.43 msec, echo time (TE) 5.25 msec, 8 views per segment, first order flow compensation, no phase-wrap, and no magnitude weighting. Also, settings of 16 NEX and maximum encoded velocity value (VENC) 60 cm/sec were used at baseline, 2 NEX and VENC 50 cm/sec immediately after onset of cuff inflation, and 8 NEX and VENC 50 cm/sec at two minutes into cuff inflation. Resulting temporal resolution for all scans was about 180 msec.

Data Analysis

Image data was imported via Scion Image (Scion Corporation, Frederick, Md.) into a spreadsheet-based (Excel, Microsoft Corporation, Mountain View, Calif.) program created in our laboratory. The cardiac phase closest to peak systole was identified by choosing the image with the greatest peak velocity and was used for further analysis. An approach modified from one by Oyre et al. (Oyre S, Ringgaard S, Kozerke S, Paaske W P, Scheidegger M B, Boesiger P, Pedersen E M. Quantitation of circumferential subpixel vessel wall position and wall shear stress by multiple sectored three-dimensional paraboloid modeling of velocity encoded cine MR. *Magn Reson Med*, 1998; 40:645-655) was used to calculate shear and radius. In our approach, the limits of the arterial diameter were estimated in two orthogonal axes. An initial estimate of the center of the cross-section was calculated from those limits. The cross-section was divided into 12 sectors around the estimated center. For each sector, outer radius of the velocity profile was estimated. A ring segment of datapoints with radius ranging from slightly less than the initially estimated outer radius to about 1 mm inward toward the estimated center was used.

The velocity pixels in the ring segment of the sector were fit by least-squares method to a parabola with the assumption that blood flow velocity at the lumen wall is zero. Shear rate was calculated as the slope of the velocity profile at the lumen-wall interface. Radius was calculated as the distance from the center of the velocity parabola to the point where the parabola crosses zero velocity. The calculated lumen radius and shear values were averaged over the 12 sectors in the arterial cross-section. This approach provides sub-pixel precision in calculating lumen radius, and was shown to be accurate when compared to glass tubes of known manufactured diameter. Furthermore, the approach is not constrained by the geometry of the lumen perimeter, i.e. the arterial cross-section does not have to be perfectly circular. Systolic flow was measured directly by summing all of the velocity pixels in the arterial cross-section. Shear rate immediately after cuff inflation was calculated using flow measured at two minutes into cuff inflation, and using radius measured at baseline, using the Poiseuille equation:

$$\text{shear rate} = 4k(\text{flow})/((\pi)(\text{radius}^3))$$

The constant k is necessary because the velocity profile during systole is slightly blunted rather than being a fully developed parabola (16-20). Consequently the true shear rate is greater than what would be calculated using a fully developed parabolic velocity profile. Thus k describes how many times greater the shear rate is than would be predicted by a fully developed paraboloid given the same radius and flow. The value of k was determined for each subject by directly measuring radius, flow, and shear rate at baseline and at 2-minutes into cuff inflation. The value of the k was solved for:

$$k = ((\pi)(\text{radius}^3))/(4(\text{flow})(\text{shear rate}))$$

The value of k at 2 minutes into cuff inflation was used in the calculation of shear rate immediately after cuff inflation. Degree of vasoconstriction was expressed as the percent change in radius from baseline to two minutes into cuff inflation.

Statistical Analysis

Results are expressed as mean value±SD. A paired t-test was used to compare measured parameters before and during cuff inflation. Linear regression analysis was used to assess the relationships between variables. A p value less than 0.05 was considered significant. To assess reproducibility of radius, shear rate, and percent constriction measurements in the eight subjects who underwent repeat scans, within-subject standard deviation was calculated.

Results

Subject characteristics and measurements are shown in Table 1-1.

TABLE 1-1

Subject Characteristics and Measurements

| Characteristic | Value |
| --- | --- |
| N | 33 (17F/16M) |
| Age, years | 27 ± 5 |
| BMI (kg/m$^2$) | 23 ± 3 |

TABLE 1-1-continued

Subject Characteristics and Measurements

| Characteristic | Value |
| --- | --- |
| Tchol, mg/dL | 172 ± 31 |
| HDL, mg/dL | 61 ± 13 |
| Trig, mg/dL | 83 ± 32 |
| LDL, mg/dL | 94 ± 27 |
| Glucose, mg/dL | 81 ± 9 |
| Hematocrit, % | 42 ± 3 |
| Shear Rate, Baseline (sec$^{-1}$) | 404 ± 78 |
| Shear Rate at 0' into C.I. (sec$^{-1}$) | 233 ± 75* |
| Shear Rate at 2' into C.I. (sec$^{-1}$) | 252 ± 75*† |
| Radius, Baseline (mm) | 3.52 ± .41 |
| Radius at 2' into C.I. (mm) | 3.43 ± .42* |
| % Change in Radius | −2.8 ± 2.5 |

Values represent mean ± SD. F = females; M = males; BMI = body mass index; Tchol = total cholesterol; HDL = high-density lipoprotein; Trig = triglycerides; LDL = low-density lipoprotein; C.I. = cuff inflation;
*p < .0001 vs. baseline;
†p < .0001 vs. 0' into cuff inflation.

Figure 8:
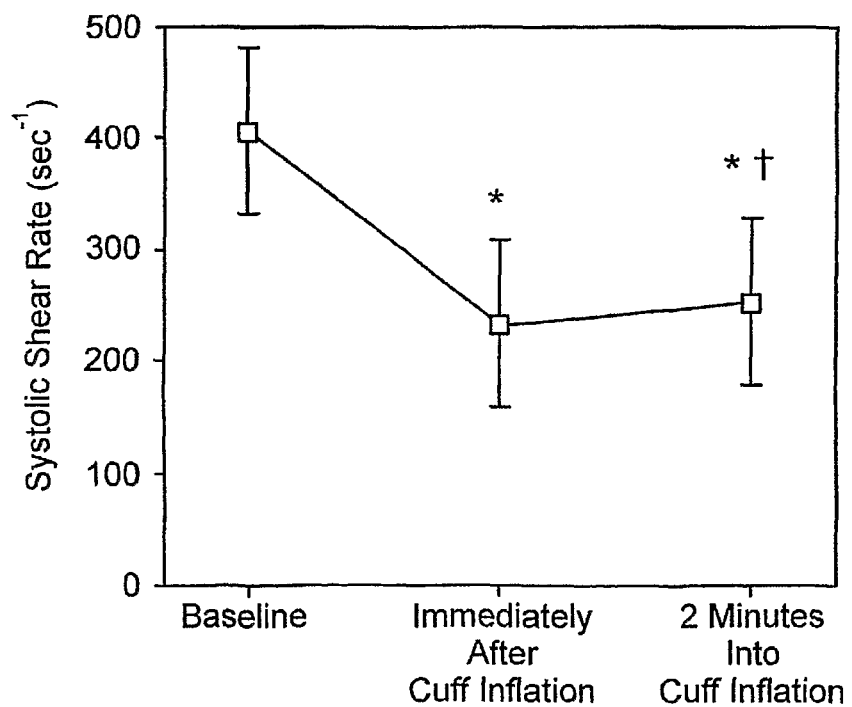
FIG. 8 is graphical view of time-course of systolic shear rate in the femoral artery at baseline, immediately after cuff inflation, and at two minutes into cuff inflation. *P<0.0001 vs baseline, †P<0.0001 vs Immediately After Cuff Inflation.
Figure 7A:
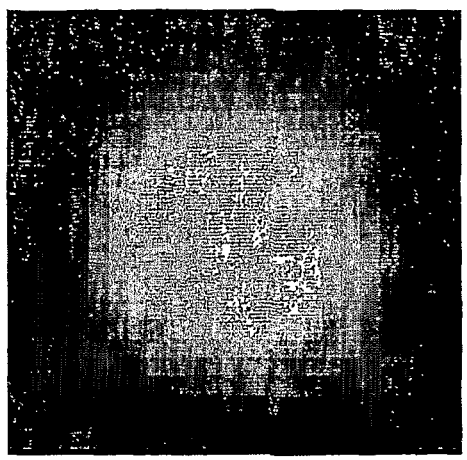
FIG. 7A is a velocity-encoded phase contrast magnetic resonance image of the cross-section during systole for a typical femoral artery at Baseline.
Figure 7B:
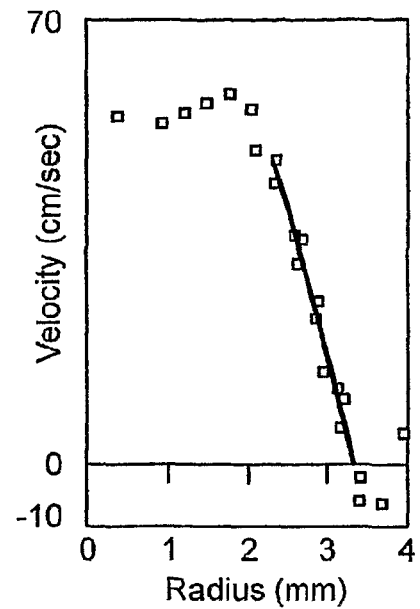
FIG. 7B is a graphical plot of systolic velocity versus radius for one of 12 sectors around the arterial circumference at Baseline.
Figure 7C:
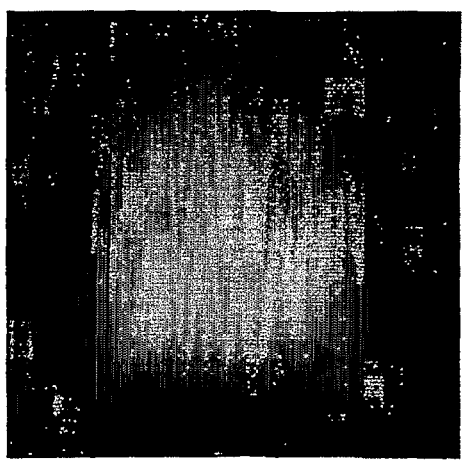
FIG. 7C is a velocity-encoded phase contrast magnetic resonance image of the cross-section during systole for a typical femoral artery at two minutes into cuff inflation (Low Flow)
Figure 7D:
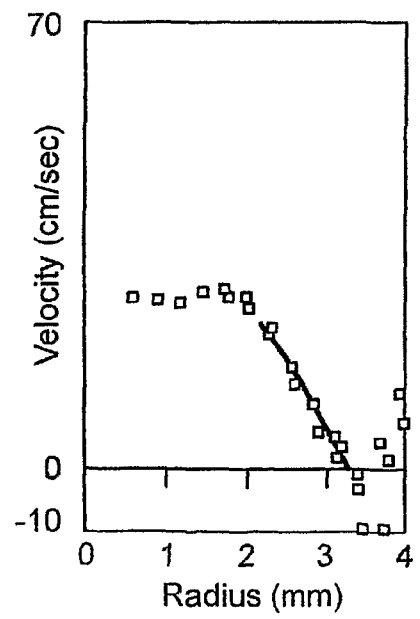
FIG. 7D is a graphical plot of systolic velocity versus radius for one of 12 sectors around the arterial circumference at two minutes into cuff inflation (Low Flow)

FIGS. 7A, C show phase contrast images of a typical femoral artery at baseline and at two minutes into cuff inflation. FIGS. 7B, D follow each respective image, which figures show a surface plot of the velocity profile and a plot of velocity versus radius for one of 12 sectors around the arterial circumference. Shear rate decreased from 404±78 sec$^{-1}$ at baseline to 233±75 sec$^{-1}$ immediately after cuff inflation (p<0.0001), then recovered partially to 252±75 sec$^{-1}$ at two minutes into cuff inflation (p<0.0001, FIG. 8). Arterial radius decreased from 3.52±0.41 mm at baseline to 3.43±0.42 mm at two minutes into cuff inflation (p<0.0001). The average percent change in radius from baseline to two minutes into cuff inflation was −2.8±2.5%. The percent change in radius from baseline to two minutes into cuff inflation was proportional to the percent change in shear rate from baseline to immediately after cuff inflation (r=0.36, p=0.028, FIG. 9). Also, the absolute change in radius from baseline to two minutes into cuff inflation was proportional to the percent change in shear rate from baseline to immediately after cuff inflation (r=0.44, p=0.0097). The ratio of % change in radius divided by the % change in shear rate was greater for women than for men (0.091±0.072 vs. 0.054±0.054, p=0.049). However, this ratio was inversely related to baseline radius (p=0.040, r=0.39, FIG. 10), and baseline radius was smaller in women than in men (3.29±0.33 mm vs. 3.78±0.34 mm, p=0.0001). The constant k in the Poiseuille relationship was slightly greater at two minutes into cuff inflation than at baseline, 1.14±0.08 vs. 1.18±0.12 (p=0.035), suggesting that the velocity profile was slightly more blunted during cuff inflation.

For scans repeated on a second occasion, the average time between sessions was 125±66 days (range 48 to 255 days). The repeated measurement, within-subject standard deviation of baseline radius was 0.13 mm; radius at 2 minutes into cuff inflation, 0.14 mm; baseline shear rate, 35 sec$^{-1}$; shear rate immediately after onset of cuff inflation, 35 sec$^{-1}$. The repeated measurement, within-subject standard deviation of percent change in radius was 1.6%.

Discussion

This example shows that; (1) the reduction in shear rate during low-flow in peripheral arteries and the resulting decrease in radius can be measured using PCMRI, and (2) the percent decrease in radius is proportional to the percent reduction in shear rate. The stimulus-response relationship in low-flow mediated vasoconstriction may add useful information to the assessment of endothelial function.

Figure 9:
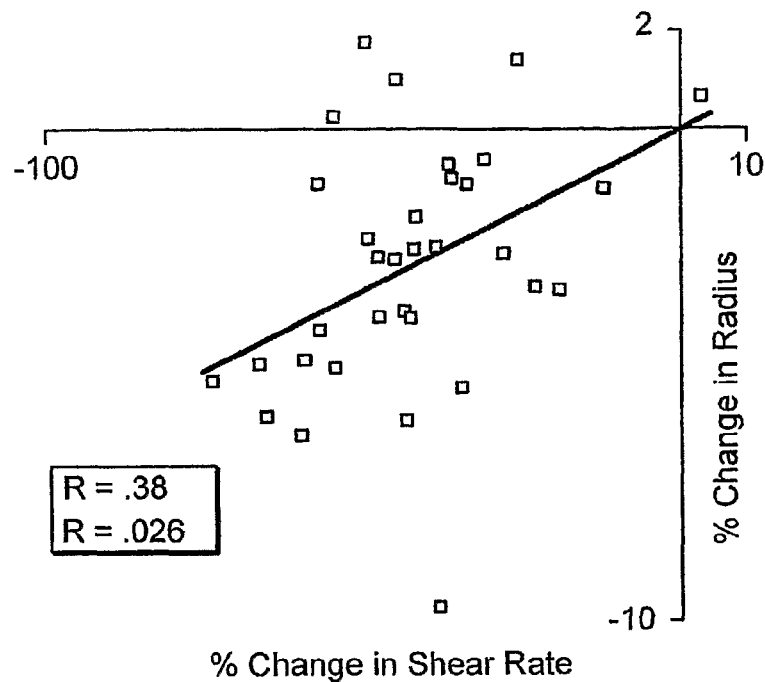
FIG. 9 is a graphical view of percent reduction in radius at two minutes into cuff inflation is proportional to the percent reduction in shear rate at the onset of cuff inflation.
Figure 10:
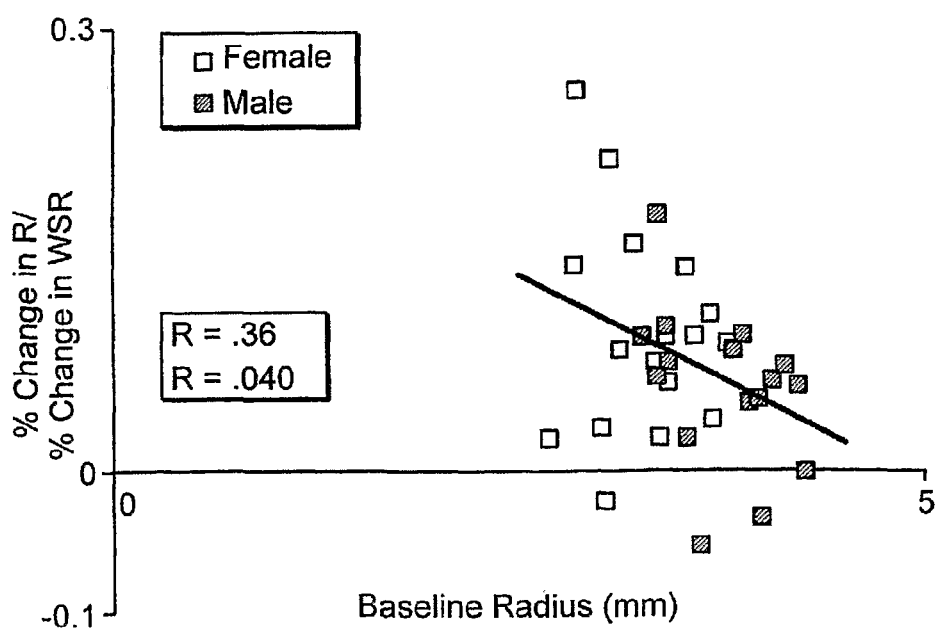
FIG. 10 is a graphical view showing that the ratio of % Change in Radius (R) to % Change in Wall Shear Rate (WSR) is inversely related to Baseline Radius (the dependence of the ratio on arterial size may explain why the ratio is greater in women than in men)

Low-flow mediated vasoconstriction in peripheral arteries has been measured using ultrasound, but has been studied much less extensively than hyperemia-induced dilation. Vasoconstriction was seen in response to reduced flow in hypercholesterolemic subjects but not in normocholesterolemic controls. In fact the degree of reduction was closely related to the degree of elevation of blood cholesterol and of its low density lipoprotein fraction. Cholesterol lowering therapy reduced the degree of vasoconstriction in hypercholesterolemic subjects. Vasoconstriction during reduced flow was detected in smokers but not nonsmokers. The stimulus-response relationship in low-flow mediated vasoconstriction may add useful information when assessing whether two different populations may be at different levels of cardiovascular risk. Levenson et al. detected no difference in brachial artery diameter reduction between men and women, but did detect a difference when the % change in diameter was normalized to the % change in shear rate (Levenson J, Pessana F, Gariepy J, Armentano R, Simon A. Gender differences in wall shear-mediated brachial artery vasoconstriction and vasodilation. *J Am Coll Cardiol,* 2001; 38:1668-1674). We also found that the normalized ratio was greater in women. However, this may be explained by the smaller arterial size in women, since we also found an inverse correlation between the normalized ratio and arterial size (FIG. 9).

The anti-atherosclerotic actions of endothelial-derived nitric oxide on promoting vasodilation, inhibiting inflammation, inhibiting platelet aggregation, and inhibiting smooth muscle proliferation are opposed by the actions of endothelin-1 (Alonso D, Radomslci M W. The nitric oxide-endothelin-1 connection. *Heart Fail Rev,* 2003; 8:107-115). Measuring the stimulus-response relationship in low-flow mediated vasoconstriction may provide additional useful information on the balance between these two mediators of atherosclerosis development.

Magnetic resonance imaging has recently been employed to assess arterial endothelial function by measuring flow mediated dilation or reactive hyperemia. A fixed cross-section can be imaged repeatedly, reducing operator dependence. An additional advantage of using velocity-encoded MRI is that flow velocity information across the entire cross-section is obtained simultaneously with dimension information, enabling calculation of the shear stimulus for vasoactivity.

An advantage of evaluating endothelial function during cuff inflation is that a steady state is reached, as opposed to the post-release period—when the hyperemia and subsequent dilation are more transient. This allows the scan duration to be longer, which enables an increased signal-to-noise ratio of the image. A recent study suggested that flow and radius do not change significantly between two and five minutes into cuff inflation. Consequently, we designed our scanning protocol to allow for a scan duration of about 2 minutes, starting at two minutes into cuff inflation, thus optimizing signal to noise ratio during the cuff inflation period.

The fact that the constant k in the Poiseuille relationship was slightly greater at two minutes into cuff inflation than at baseline suggests that the velocity profile was slightly more blunted during cuff inflation. This likely reflects the fact that flow decreased to a greater extent than radius did from baseline to two minutes into cuff inflation. A velocity profile is more blunted when arterial radius is large relative to blood flow velocity. In this case, the effect, though statistically significant, was very slight in practical terms.

We used the cardiac phase with peak flow to calculate shear rate and radius. In other cardiac phases, the signal-to-noise ratio is much lower and the flow is more complex with regard to spatial distribution in the arterial cross-section. The fact that radius was measured during systole may help to explain why an increase in radius was seen during reduced flow in some cases. Since the occlusion was distal to the imaged cross-section, there may sometimes have been increased systolic distension of the artery proximal to the occlusion. More consistent and pronounced constriction may be measured in future studies if diastolic cardiac phases are used for radius measurements, perhaps based on the magnitude images.

Signal-to-noise ratio of the phase contrast images during cuff inflation is reduced compared to baseline because of reduced flow velocities. Therefore we did not rely on a rapid scan immediately after cuff inflation to directly measure shear rate at that time. However, we did directly measure flow immediately after cuff inflation in a subset of 12 subjects, to evaluate whether it differed consistently from flow measured at 2 minutes into cuff occlusion. The duration of the scans started immediately after cuff inflation were approximately 35 seconds. Flow measured during the scans started immediately after cuff inflation was not different from flow measured starting at 2 minutes into cuff inflation (p=NS).

Example 2

Methods

The superficial femoral artery was studied in 20 men—10 men with no risk factors aged 20-33 years, and 10 men with atherosclerotic risk factors including type II diabetics and older age, 52-69 years. A receiver coil was placed on the upper thigh, and an occluding cuff was placed distal to the receiver coil. A fixed cross-section of the artery was imaged before and during a distal occlusion. An ECG-gated PCMRI sequence was used, with 10 square cm field-of-view, matrix size 256×128, 3 mm slice thickness, VENC 60 cm/sec in the S/I direction, TR 11.4 msec, 8 views per segment, and temporal resolution 182 msec. A user-independent algorithm was employed to locate the precise center of the arterial cross-section in the magnitude image by optimizing the correlation of datapoints in a radial plot. A smoothed average of the optimized radial plot of the data was calculated. The radius of the artery was defined using the full-width, half-maximum approach (Hoogeveen R M, Bakker C J, Viergever M A. *J Magn Reson Imaging*. 1998; 8:1228-1235). To calculate shear rate, velocity pixels of a radial plot near the lumen wall was fit by least-squares method to a parabola, with the assumption that blood flow velocity at the lumen wall is zero (Oyre S, Ringgaard S, Kozerke S, et al. *Magn Reson Med*. 1998; 40:645-655). Shear rate was calculated as the slope of the velocity profile at the lumen-wall interface. Background correction was used in both the magnitude and phase plots. Shear rate and radius were averaged throughout the cardiac cycle.

Results

FIGS. 11A-D show baseline magnitude and phase images at peak systole, and their corresponding radial plots for a typical control subject. The groups did not differ with respect to baseline radius or shear rate (p=NS). There was a nonsignificant trend of a smaller change in shear (−67±31 vs. −82±36 sec$^{-1}$, p=0.17) and % change in shear (−49±21 vs. −59±11%, p=0.10) from baseline to 2 minutes into occlusion in the older diabetics compared with controls. From baseline to 2 minutes into distal occlusion, radius decreased in the controls (3.24±36 mm vs. 3.08±0.32 mm, p=0.0002) but not in the older diabetics (3.29±0.32 mm vs. 3.30±34 mm, p=NS). The % change in radius was −4.9±2.7% in the controls vs. 0.4±1.7% in the older diabetics (p<0.0001).

Conclusions

Differences in peripheral arterial constriction during reduced shear can be measured using PCMRI and low-shear mediated constriction is impaired in older diabetics compared with a group without these risk factors. Measuring low-shear mediated peripheral vasoconstriction using PCMRI may add useful information to the noninvasive evaluation of arterial endothelial function.

Example 3

In this study, we sought to determine shear-related aspects of femoral arterial reactivity that distinguish healthy men from men with vascular risk factors known to be associated with impaired endothelial function, including older age and type 2 diabetes.

Study Participants.

Twenty male subjects were studied. Ten were controls, aged 20-33, with no cardiovascular risk factors including hypertension, diabetes, hyperlipidemia, smoking, obesity or cardiac disease in a first-degree relative. Ten had risk factors for atherosclerosis including older age, 52-69 years, and type 2 diabetes. Risk factors excluded from the at-risk group were smoking, known vascular disease, and a body mass index greater than 33. None of the at-risk group had symptoms of claudication. No subject was acutely ill. The study protocol was approved by the Institutional Review Board at the Johns Hopkins School of Medicine. All subjects gave written informed consent.

Study Protocol

Subjects abstained from eating or drinking except water for at least 6 hours before the study. No subject was asked to stop any medicine before a scan, except for morning hypoglycemic agents, and none was on a nitrate medicine. All scans were performed in the morning. Baseline blood pressure was recorded in the right arm. PCMRI was performed using a 1.5T scanner (CV/i, General Electric Medical Systems, Milwaukee, Wis.) equipped with cardiac gradient coils (40 mT/m, 120 T/m/s). Electrocardiographic leads were placed on the thorax. A dual cardiac phased array receiving coil was placed anterior and posterior to the upper thigh. An inflatable cuff was placed on the lower thigh. Phase-contrast images were obtained at baseline. The cuff was inflated at least 20 mmHg above the subject's measured systolic blood pressure for 5 minutes, then released. Images using the same fixed cross-sectional axial prescription as at baseline were obtained at two minutes into cuff inflation, immediately after release, and at one minute after release. Serum values of glucose, hematocrit, and fasting lipid panel were obtained after the scanning portion of the study. Hemoglobin A IC was measured in the at-risk group. To assess the reproducibility of measurements, the study was repeated in each of four control subjects during a second session.

Imaging Protocol

Coronal and axial scout images were obtained to locate the superficial femoral artery and to verify that the artery was parallel to the magnet bore. Phase contrast scans were gated to the electrocardiogram signal. A single imaging plane perpendicular to the artery of interest was prescribed. The imaging parameters were: Matrix size 256×128, field-of-view 10 by 10 cm, slice thickness 3 mm, flip angle 25 degrees, bandwidth 31.2 kHz, repetition time (TR) 11.43 msec, echo time (TE) 5.25 msec, 8 views per segment, first order flow compensation, no phase-wrap, and no magnitude weighting. Settings of 16 signal averages (NEX) were used at baseline, and 8 NEX at two minutes into cuff inflation. During peak hyperemia, 10 views per segment was used if necessary to keep the scanning time at 35 seconds or less. Maximum encoded velocity (VENC) was 60-70 cm/sec during baseline, 120-150 cm/sec during peak hyperemia, and 80-100 cm/sec at one minute after cuff release. Resulting temporal resolution for all scans was about 180 msec. Each scan provided magnitude (anatomic) and phase (velocity) images of the arterial cross-section.

Data Analysis

Inage data was imported via Scion Image (Scion Corporation, Frederick, Md.) into a spreadsheet-based (Excel, Microsoft Corporation, Mountain View, Calif.) program created in our laboratory. The program employs a user-independent algorithm to measure arterial radius from the magnitude images, and to measure blood flow and shear rate from the phase images. The variables were measured in each phase of the cardiac cycle, and then averaged. The algorithm located the precise center of the arterial cross-section in the magnitude image by optimizing data correlation in a radial plot. A smoothed average of the optimized radial plot of the data was calculated. The radius of the artery was defined using the full-width, half-maximum approach—a well established decision rule, where the distance from the center at which the magnitude decreases to half of the its peak value is chosen as the radius. Systolic radius was defined as the maximum radius among the cardiac phases. The located center of the magnitude image was used as the center of the phase image. Flow was calculated by summing the velocity pixels inside the radius of the artery. An approach simplified from Oyre et al. was used to calculate shear rate. A one-millimeter wide segment of velocity pixels in the radial plot near the lumen wall was fit by least-squares method to a parabola, with the assumption that blood flow velocity at the lumen wall is zero. The outer edge of the segment was chosen to be where the absolute value of a smoothed average of the velocity profile decreased to 20% of its peak value. Shear rate was calculated as the slope of the velocity profile at the lumen-wall interface. This approach provides sub-pixel precision in determining shear rate and radius. Furthermore, the approach is not constrained by the geometry of the lumen perimeter, i.e. the arterial cross-section does not have to be perfectly circular. Systolic shear rate was defined as the shear rate of the cardiac phase containing highest flow.

Statistical Analysis

Results are expressed as mean value±SD. T-testing was used to compare measured parameters before, during, and after cuff inflation, and to compare variables between two groups. Linear regression analysis was used to assess relationships between variables. A p value less than 0.05 was considered significant. To assess reproducibility of measurements, within-subject standard deviation was calculated for radius, change in radius, % change in radius, shear rate, change in shear rate, and percent change in shear rate in the four subjects who underwent repeat scans.

Results

Baseline characteristics and serum laboratory values are shown in Table 3-1.

TABLE 3-1

Subject Characteristics and Serum Measurements

| | Measuremen | | |
|---|---|---|---|
| Characteristic | Controls | Older Diabetics | P value |
| Number of subjects | 10 | 10 | <.0001 |
| Age, yrs | 24 ± 4 | 64 ± 6 | <.0001 |
| Body Mass Index, kg/m$^2$ | 23.8 ± 2.8 | 26.6 ± 3.8 | .004 |
| Systolic BP, mmHg | 114 ± 12 | 133 ± 18 | .006 |
| Diastolic BP, mmHg | 73 ± 8 | 74111 | .41 |
| Glucose, mg/dl | 84 ± 7 | 144 ± 33 | .0001 |
| Total Cholesterol, mg/dl | 162 ± 34 | 180 ± 41 | .14 |
| Triglycerides, mg/dl | 94 ± 35 | 112 ± 37 | .13 |
| HDL, mg/dl | 54 ± 10 | 60 ± 15 | .17 |
| LDL, mg/dl | 89 ± 33 | 98 ± 30 | .25 |
| Hematocrit, % | 45.9 ± 1.8 | 42.8 ± 1.4 | .0002 |

Values are mean ± SD; BP indicates blood pressure; HDL, high density lipoprotein; LDL, low density lipoprotein; P value refers to comparison between groups Besides being older and having higher serum glucose, the older diabetics had higher systolic blood pressure, higher body-mass-index, and lower hematocrit. However, the hematocrit for every older diabetic subject was still in the normal range.

Reduced-Shear Mediated Vasoconstriction

Measured variables during low-flow mediated constriction are shown in Table 3-2.

TABLE 3-2

Low-Flow Mediated Constriction: Magnetic Resonance Imaging Measurements Before and During Distal Occlusion:

| Measurement | Controls (n = 10) | Older Diabetics (n = 10) | P-value between groups |
|---|---|---|---|
| Average Radius at Baseline, mm | 3.24 ± 0.36 | 3.29 ± 0.32 | .38 |
| % Change in Average Radius | −5.5 ± 3.3 | 0.4 ± 1.7 | <.001 |
| Systolic Radius at Baseline, mm | 3.46 ± .37 | 3.48 ± .30 | .43 |
| % Change in Systolic Radius | −1.7 ± 2.3 | 1.2 ± 2.2 | .0053 |
| Diastolic, Radius at Baseline, mm | 2.81 ± .32 | 2.97 ± .39 | .17 |
| % Change in Diastolic Radius | −12.2 ± 8.6 | −1.9 ± 7.0 | .0047 |
| Average Shear Rate at Baseline, sec$^{-1}$ | 134 ± 42 | 143 ± 52 | .35 |
| Change in Average Shear Rate, sec$^{-1}$ | −88 ± 41 | −67 ± 31 | .17 |
| % Change in Average Shear Rate | −61 ± 14 | −49 ± 21 | .075 |
| Systolic Shear Rate at Baseline, sec$^{-1}$ | 445 ± 73 | 394 ± 99 | .22 |

TABLE 3-2-continued

Low-Flow Mediated Constriction: Magnetic Resonance Imaging
Measurements Before and During Distal Occlusion:

| Measurement | Controls (n = 10) | Older Diabetics (n = 10) | P-value between groups |
|---|---|---|---|
| Change in Systolic Shear Rate, sec$^{-1}$ | −170 ± 72 | −62 ± 65 | .0011 |
| % Change in Systolic Shear Rate | −38 ± 14 | −16 ± 19 | .0043 |
| Average Flow at Baseline, ml/min | 284 ± 111 | 305 ± 90 | .32 |
| Change in Average Flow, mUmin | −179 ± 91 | −153 ± 83 | .26 |
| % Change in Average Flow | −61 ± 10 | −49 ± 19 | .047 |
| Systolic Flow at Baseline, ml/min | 914 ± 186 | 859 ± 88 | .21 |
| Change in Systolic Flow, ml/min | −381 ± 126 | −131 ± 230 | .0047 |
| % Change in Systolic Flow | −42 ± 13 | −15 ± 26 | .0067 |

Values are mean ± SD

The groups did not differ with respect to baseline average radius or baseline shear rate. Average radius decreased in controls (3.26±0.33 to 3.08±0.33 mm, p=0.0002) but not in the older diabetics (3.29±0.32 to 3.30±0.34 mm, p=0.47) from baseline to 2 minutes into occlusion. The % change in average radius was −5.5±3.3% in the controls vs. 0.4±1.7% in the older diabetics (p<0.0001). However, the change in systolic shear rate and the % change in systolic shear rate were also significantly less in the older diabetics. The % change in average radius was proportional to % change in systolic shear rate in the control group (p=0.024, r=0.68), and in the older diabetics (p=0.044, r=0.65, FIG. 12). However, the stimulus-response relationship was different between the two groups, in that constriction was greater in controls for a given stimulus.

Hyperemia Mediated Vasodilation

Measured variables during hyperemia mediated dilation are shown in Table 3-3.

betics with regard to hyperemic shear rate, change in shear rate, and % change in shear rate from baseline to peak hyperemia. There were also significant differences with regard to hyperemic flow, change in flow, and % change in flow from baseline to peak hyperemia. The two groups were completely distinguished from each other by each of three measurements: hyperemic average shear rate (FIGS. 13A,B), change in average shear rate, and change in systolic shear rate from baseline to peak hyperemia. FIG. 13A show average flow versus baseline average radius squared. At baseline, average flow is proportional to average radius squared for all subjects. However, during peak hyperemia, the proportionality only holds for the controls (FIG. 13B).

Discussion

As seen from the foregoing, both hyperemia-mediated vasodilation and low-flow mediated vasoconstriction are impaired in older diabetic men compared with young controls. Secondly, hyperemic shear rate was lower in older dia-

TABLE 3-3

Flow Mediated Dilation: Magnetic Resonance Imaging
Measurements Before and After Occlusion Release

| Measurement | Controls (n = 10) | Older Diabetics (n = 10) | P-value between groups |
|---|---|---|---|
| Average Radius at Baseline, mm | 3.24 ± .36 | 3.29 ± .32 | .38 |
| % Change in Average Radius | 1.08 ± 2.27 | −.99 ± 3.15 | .056 |
| Systolic Radius at Baseline, mm | 3.46 ± .37 | 3.48 ± .30 | .43 |
| % Change in Systolic Radius | 1.8 ± 2.0 | −0.4 ± 2.1 | .016 |
| Diastolic Radius at Baseline, mm | 2.81 ± .32 | 2.97 ± .39 | .17 |
| % Change in Diastolic Radius | −1.1 ± 9.4 | −4.0 ± 8.8 | .24 |
| Average Flow at Baseline, ml/min | 284 ± 111 | 305 ± 90 | .32 |
| Average Flow during Peak Hyperemia, ml/min | 1379 ± 342* | 773 ± 153* | .00013 |
| Change in Average Flow, ml/min | 1095 ± 286 | 468 ± 150 | <.0001 |
| % Change in Average Flow | 79.3 ± 6.5 | 59.7 ± 13.4 | .00058 |
| Average Shear Rate at Baseline, sec$^{-1}$ | 134 ± 42 | 143 ± 52 | .35 |
| Average Shear Rate during Peak Hyperemia, sec$^{-1}$ | 587 ± 69* | 302 ± 81* | <.0001 |
| Change in Average Shear Rate, sec$^{-1}$ | 453 ± 82 | 159 ± 51 | <.0001 |
| % Change in Average Shear Rate | 76.8 ± 7.9 | 52.7 ± 12.1 | <.0001 |
| Systolic Shear Rate at Baseline, sec$^{-1}$ | 445 ± 73 | 394 ± 99 | .10 |
| Systolic Shear Rate during Peak Hyperemia, sec$^{-1}$ | 895 ± 123* | 525 ± 128† | <.0001 |
| Change in Systolic Shear Rate, sec$^{-1}$ | 450 ± 87 | 131 ± 91 | <.0001 |
| % Change in Systolic Shear Rate | 50 ± 6 | 24 ± 14 | <.0001 |

Values are mean ± SD
*p < .0001;
†p < .01; Baseline vs. Peak Hyperemia

There was a significant difference between controls and older diabetics with regard to % change in systolic radius. There was also a difference in % change in average radius that did not quite achieve statistical significance. There were highly significant differences between controls and older diabetics, and this measurement completely distinguished the two groups. Thirdly, low-flow-mediated constriction was proportional to % change in systolic shear rate in each group, but the degree of constriction in the older diabetics was less for a given shear reduction.

As can be seen from the foregoing example, there are several implications revealed. First, measuring systolic shear rate during reactive hyperemia in the femoral artery may be a sensitive method for identifying subjects with vascular dysfunction. In our study, it was more sensitive and specific than flow-mediated dilation. The utility of this parameter should be investigated in other populations with known vascular dysfunction. Another implication of this study is that measuring arterial constriction during reduced shear may be useful for identifying vascular dysfunction.

A third implication concerns the development of atherosclerosis. Lower shear rate is associated with atherosclerosis development. Shear rate is dependent on flow and inversely dependent on radius cubed. Baseline flow, dimension, and shear were similar between groups in this study. However, during hyperemia, flow and therefore shear rate was less in the older diabetics. It may be that the femoral artery in older diabetics experiences lower peaks in shear rate throughout daily activity due to lower levels of hyperemia. Thus, although the dimension of an artery may be suited to its resting flow, this dimension may be relatively larger than it needs to be during hyperemia in older diabetics.

Procedural Considerations

Regarding shear-mediated dilation, the within-subject variability of repeated hyperemic shear measurement was lower than that of % change in radius (Table 3-4). This may be part of the reason why hyperemic shear was a better discriminating parameter between the two groups in our study. However, the variability of % change in radius was similar to some ultrasound studies. The discriminating potential of hyperemic shear compared with % change in dimension should be investigated using ultrasound as well.

Studies of flow-mediated dilation have used either proximal or distal occlusion. By using distal occlusion, we were able to study conduit shear and radius changes during the period of reduced flow. Unlike flow mediated dilation, where the stimulus is transient, the shear rate and radius during distal occlusion reach a steady-state after about 2 minutes. This allows the measurement of variables during a period when they are not changing significantly. This is particularly helpful in MRI, where a longer duration scan can be used to obtain a greater signal-to-noise ratio.

Figure 12:
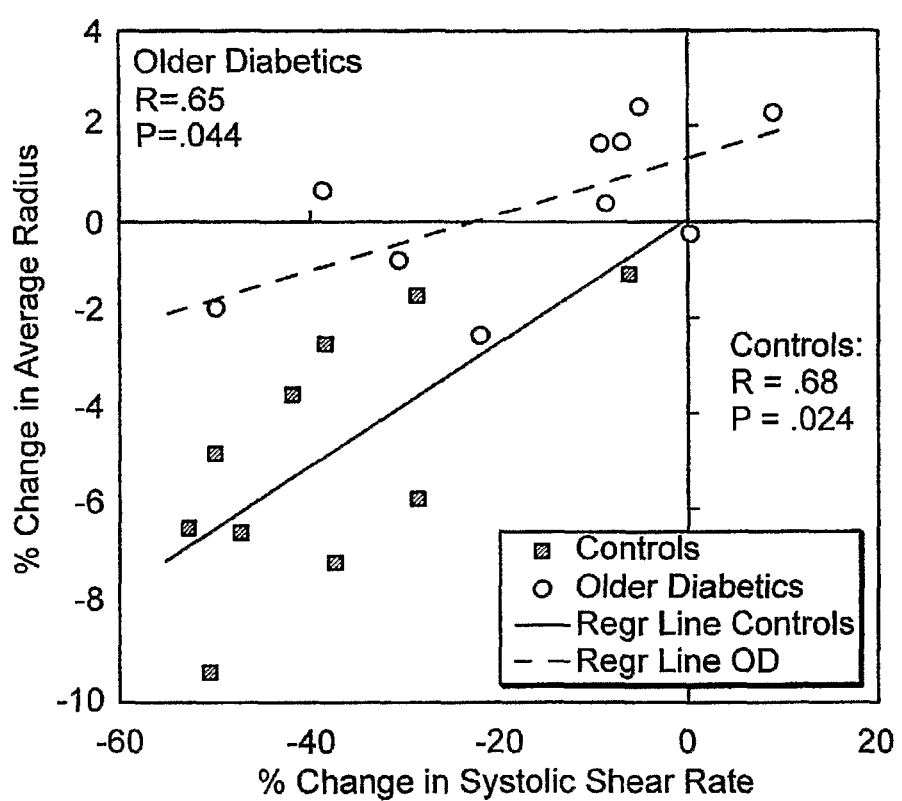
FIG. 12 is a graphical plot of % change in average radius versus % change in systolic shear rate.

Although the full-width, half maximum decision rule for defining arterial radius from a magnitude image is standard in MRI, different results may arise between this approach and another standard approach, such as defining radius in the velocity image to be where the best-fit parabola would have a velocity of zero (FIG. 12). However, it is the change in radius that defines the constriction response, so theoretical differences between the two approaches are probably negligible for the purposes of this study. Baseline radius does factor in the calculation of percent change in radius, but the relationship between % change in shear rate vs. % change in radius was quite similar to the relationship between % change in shear rate and absolute change in radius. The advantage of using the magnitude images is that the signal-to-noise ratio varies much less than the that of the phase images throughout the cardiac cycle.

Although all hematocrit values were normal in the older diabetics, the average hematocrit was lower than in the controls. Hematocrit is a determinant of viscosity, which combines with shear rate to determine shear stress, the stimulus for flow-mediated vasoactivity. This could suggest that differences in the shear stress stimulus may be even greater than indicated by our measurement of shear rate alone. However, overall plasma viscosity is higher in type 2 diabetics.

Mechanisms Explaining Differences in Low-Flow Mediated Constriction

Low-flow-mediated constriction is dependent on endothelin-1 acting via endothelin-A receptors. The constrictive effect of endogenous endothelin-1 is impaired in diabetics, possibly due to a down-regulation of endothelin-A receptors. This may explain why low-flow mediated constriction was impaired in the older diabetics in our study. However, the reduction in systolic shear rate, the stimulus for constriction, was also less in the older diabetic group due at least in part to the smaller reduction in systolic flow. The smaller reduction in systolic flow may reflect endothelial-dependent or independent resistance vessel dysfunction. Another possible reason for lower reduction in flow would be lower relative flow to the distal leg in older diabetics and therefore less relative flow to exclude with distal occlusion. Blood flow to the leg has been measured to be lower in the elderly because of increased sympathetic tone and not because of differences in muscle mass.

Another possible contributing explanation for less constriction in older diabetics would be if conduit smooth muscle constriction were impaired in that group. We did not test for differences in endothelial-independent constriction by infusing a direct arterial smooth muscle vasoconstrictor. However, previous studies have demonstrated that constrictor responses to direct smooth muscle vasoconstricting agents are equivalent in older humans arteries and are equivalent or even enhanced in diabetic human arteries.

Example 4

Methods

Using magnetic resonance imaging, we directly measured shear rate at rest and during reactive hyperemia (endothelial-dependent) in brachial and femoral arteries of 46 subjects—14 young (21-33 yrs) healthy (YH), 18 older (>50 yrs) healthy (OH), and 14 older type 2 diabetic (OD) subjects. Change in systolic shear rate (ΔSSR) from baseline to peak hyperemia was calculated. Leg endothelial function relative to arm was assessed by ΔSSR-leg/ΔSSR-arm.

Figure 15:
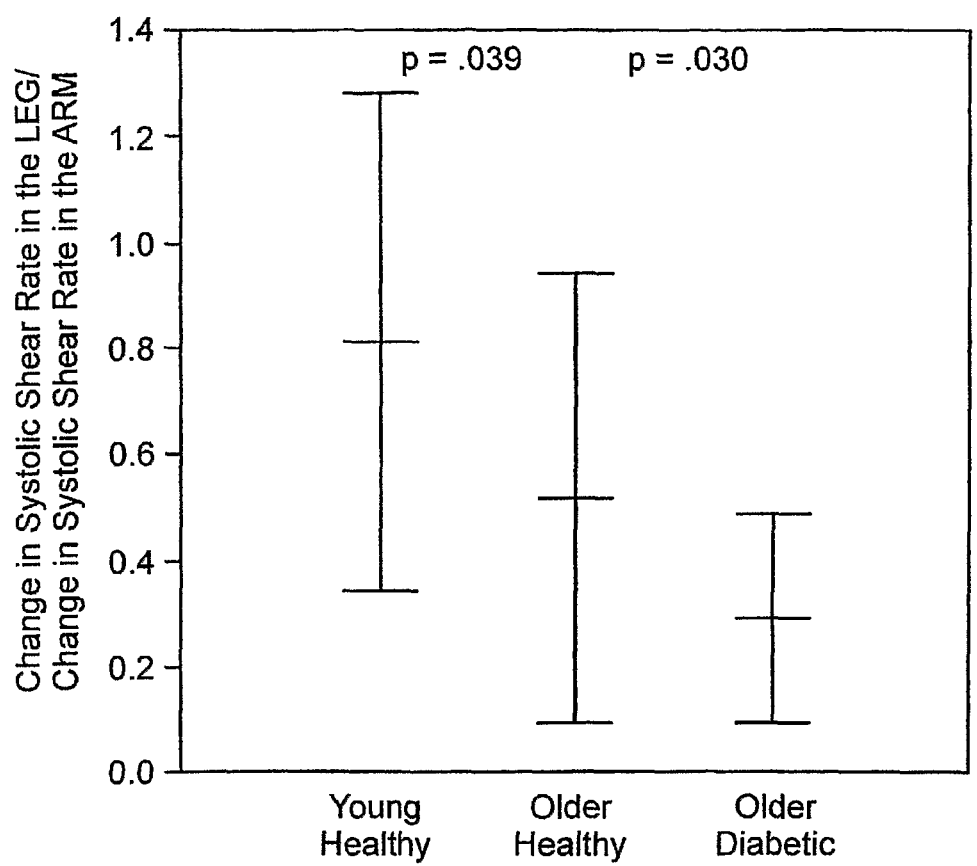
FIG. 15 is a graphical figure illustrating change in systolic shear rate in the leg/change in systolic shear rate in the arm for young healthy, older healthy and older diabetic men.

Results:

The groups were similar with regard to resting femoral radius, brachial radius, femoral shear rate, ratio of femoral-to-brachial radius, and ratio of femoral-to-brachial shear rate. Resting brachial shear rate was lower in OH than YH (358±110 vs 441±137 $sec^{-1}$, p=0.04), but there were no differences between groups during hyperemia. During hyperemia, ΔSSR-leg/ΔSSR-arm was lower in OD (0.29±0.20) than OH (0.52±0.42, p=0.030), and lower in OH than YH (0.82±0.47, p=0.039, FIG. 15).

Conclusions:

Endothelial vasodilator function is increasingly more impaired in the leg than in the arm with increasing level of cardiovascular risk. Differences in regional endothelial function may underlie differences in atherosclerosis development in different arterial beds.

Example 5

Study Participants

Twenty male subjects were studied: Ten were healthy controls, aged 20-33, with no cardiovascular risk factors including hypertension, diabetes, hyperlipidemia, smoking, obesity or cardiac disease in a first-degree relative. Ten were older healthy men, ages 50-74, with otherwise no cardiovascular risk factors. No participant was treated with cardiovascular medicines, had symptoms of claudication, or was acutely ill. The study protocol was approved by the Institutional Review Board at the Johns Hopkins School of Medicine. All subjects gave written informed consent.

Study Protocol

Subjects abstained from eating or drinking except water for at least 6 hours before the study. All scans were performed in the morning. Baseline blood pressure was recorded in the right arm. Phase contrast MRI was performed using a 1.5T scanner (CV/i, General Electric Healthcare Technologies, Milwaukee, Wis.) equipped with cardiac gradient coils (40 mT/m, 120 T/m/s). Electrocardiographic leads were placed on the thorax. A four-element phased array receiving coil was placed anterior and posterior to the upper thigh. An inflatable cuff was placed on the lower thigh. Phase-contrast images were obtained at baseline. The cuff was inflated at least 30 mmHg above the subject's measured systolic blood pressure for 5 minutes, then released. Images using the same fixed cross-sectional axial prescription as at baseline were obtained immediately after cuff release, and at one minute after release. Serum values of glucose, hematocrit, and fasting lipid panel were obtained after the scanning portion of the study. To assess the reproducibility of measurements, the study was repeated in each of four young control subjects during a second session.

Imaging Protocol

Coronal and axial scout images were obtained to locate the superficial femoral artery at 3 to 5 cm distal to the bifurcation of the common femoral artery, and to verify that the artery was parallel to the magnet bore. Phase contrast scans were gated to the electrocardiogram signal. A single imaging plane perpendicular to the artery of interest was prescribed. The imaging parameters were: Matrix size 256×128, field-of-view 10 by 10 cm, slice thickness 3 mm, flip angle 25 degrees, bandwidth 31.2 kHz, repetition time (TR) 11.43 msec, echo time (TE) 5.25 msec, 8 views per segment, first order flow compensation, no phase-wrap, and no magnitude weighting. Settings of 16 signal averages (NEX) were used at baseline, and 8 NEX after cuff release. During peak hyperemia, 10 views per segment was used if necessary to keep the scanning time at 35 seconds or less. Maximum encoded velocity (VENC) was 60-70 cm/sec during baseline, 120-150 cm/sec during peak hyperemia, and 80-100 cm/sec at one minute after cuff release. Resulting temporal resolution was about 90-180 msec. Each scan provided magnitude (anatomic) and phase (velocity) images of the arterial cross-section.

Data Analysis

Image data was imported via Scion Image (Scion Corporation, Frederick, Md.) into a spreadsheet-based (Excel, Microsoft Corporation, Mountain View, Calif.) program created in our laboratory. The program employs a user-independent algorithm to measure arterial radius from the magnitude images, and to measure blood flow and shear rate from the phase images. The variables were measured in each phase of the cardiac cycle, and then averaged. The algorithm located the precise center of the arterial cross-section in the magnitude image by optimizing data correlation in a radial plot. A smoothed average of the optimized radial plot of the data was calculated. The radius of the artery was defined using the full-width, half-maximum approach, where the distance from the center at which the magnitude decreases to half of the its peak value is chosen as the radius. Systolic radius was defined as the maximum radius among the cardiac phases. The located center of the magnitude image was used as the center of the phase image. Flow was calculated by summing the velocity pixels inside the radius of the artery. An approach simplified from Oyre et al. was used to calculate shear rate. A one-millimeter wide segment of velocity pixels in the radial plot near the lumen wall was fit by least-squares method to a parabola, with the assumption that blood flow velocity at the lumen wall is zero. The outer edge of the segment was chosen where the absolute value of a smoothed average of the velocity profile decreased to 20% of its peak value. Shear rate was calculated as the slope of the velocity profile at the lumen-wall interface. This approach provides sub-pixel precision in determining shear rate and radius, and is not constrained by the geometry of the lumen perimeter, i.e. the arterial cross-section does not have to be perfectly circular. Systolic shear rate was defined as the shear rate of the cardiac phase containing highest flow. Average shear rate was calculated from all cardiac phases. Flow mediated dilation was calculated as percent change in systolic radius from baseline to one minute after cuff release.

Statistical Analysis

Results are expressed as mean value±SD. T-testing was used to compare measured parameters before, during, and after cuff inflation, and to compare variables between two groups. Linear regression analysis was used to assess relationships between variables. A p value less than 0.05 was considered significant. To assess reproducibility of measurements, within-subject standard deviation and coefficient of variation were calculated for radius, flow, shear rate, and changes in these parameters in the four subjects who underwent repeat scans.

Results

Patient characteristics are summarized in Table 5-1.

TABLE 5-1

Subject Characteristics and Serum Measurements

| Characteristic | Measurement | | |
|---|---|---|---|
| | Younger Men | Older Men | P |
| Number of subjects | 10 | 10 | |
| Age, yrs | 24 ± 4 | 60 ± 7 | <.0001 |
| Body Mass Index, kg/m$^2$ | 23.8 ± 2.8 | 25.6 ± 3.8 | .12 |
| Systolic BP, mmHg | 114 ± 12 | 117 ± 8 | .26 |
| Diastolic BP, mmHg | 73 ± 8 | 73 ± 8 | .48 |
| Glucose, mg/dl | 84 ± 7 | 87 ± 14 | .29 |
| Total Cholesterol, mg/dl | 162 ± 34 | 199 ± 28 | .008 |
| Triglycerides, mg/dl | 94 ± 35 | 107 ± 49 | .24 |
| HDL, mg/dl | 54 ± 10 | 58 ± 7 | .19 |
| LDL, mg/dl | 89 ± 33 | 120 ± 29 | .02 |
| Hematocrit, % | 45.9 ± 1.8 | 44.8 ± 2.8 | .16 |

Figure 16A:
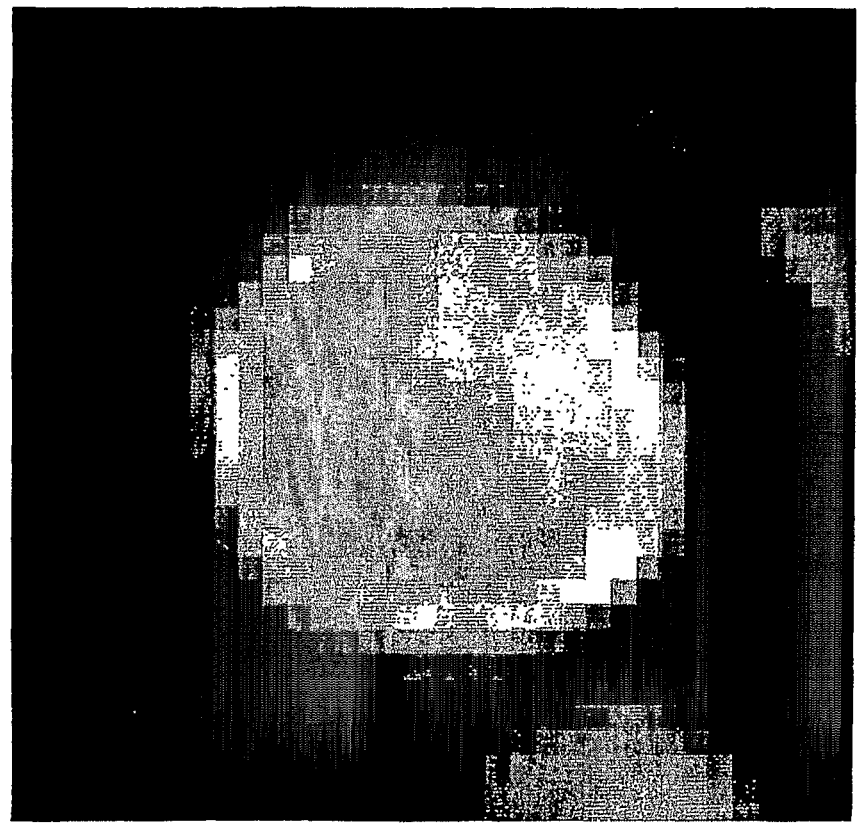
FIG. 16A is an illustrative view of a phase contrast MRI magnitude component of a baseline femoral arterial cross-section in a typical young, healthy subject
Figure 16B:
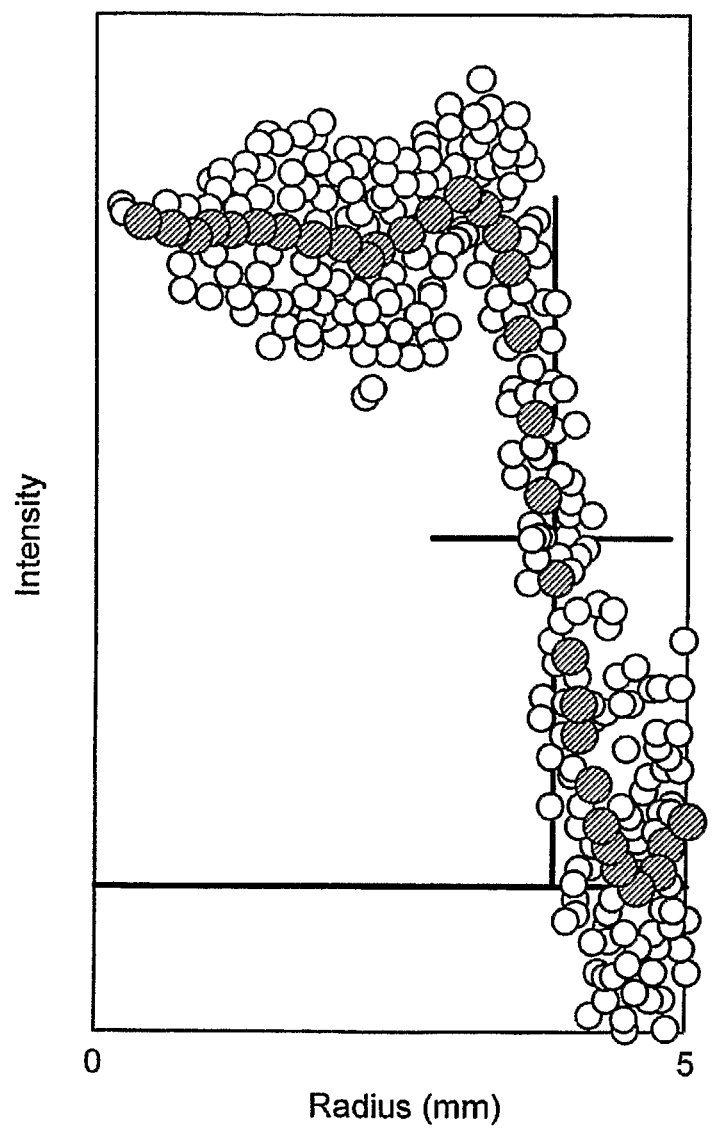
FIG. 16B is a plot of the intensity datapoints (open circles) versus their distance from the optimal center of the cross-section. The plot also shows a smoothed average (closed circles) of the intensity datapoints. The cross-hatch indicates where the intensity decreases to half its peak. This is defined as the radius of the artery (full-width, half-max method).
Figure 17A:
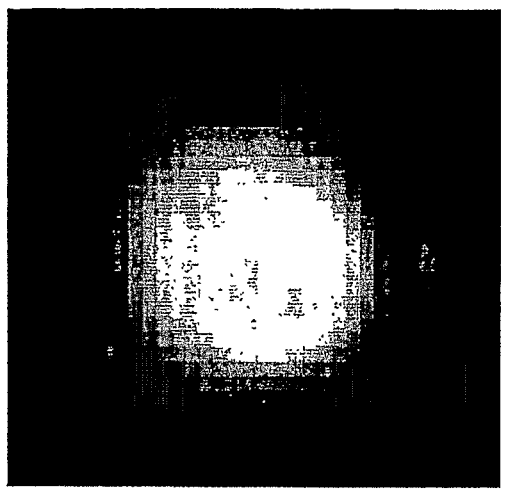
FIGS. 17A,C are phase contrast MRI phase components of a baseline femoral arterial cross-section in the same subject as in FIG. 16A, where
Figure 17B:
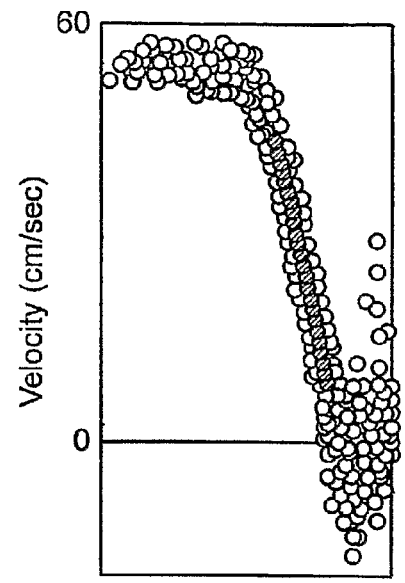
FIGS. 17B,D are each a plot of the velocity datapoints (open circles) versus their distance from the optimal center of the cross-section for FIGS. 16A,C respectively. The plot also shows the parabola segment that is best-fit to the datapoints near the arterial wall. The slope of the best-fit parabola where it reaches zero is shear rate.
Figure 17C:
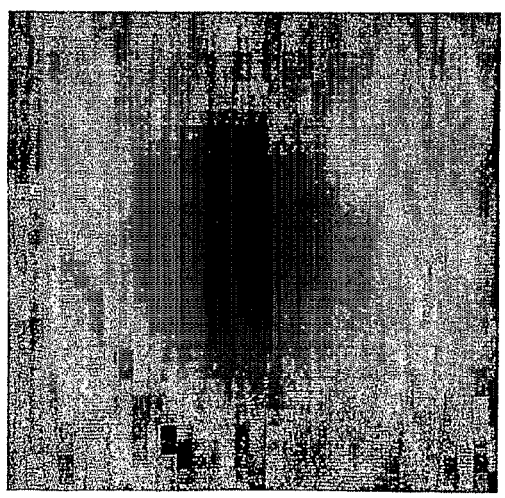
Figure 17D:
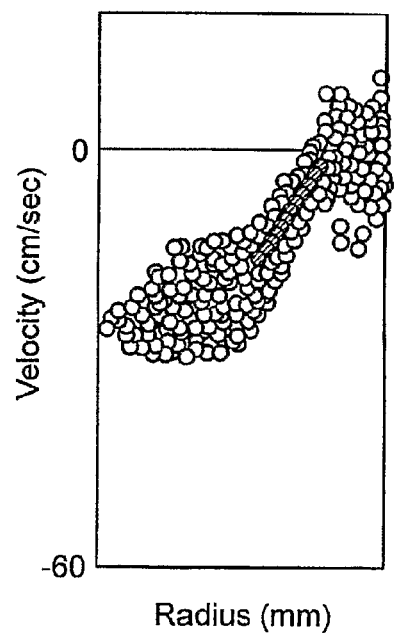
Figure 18B:
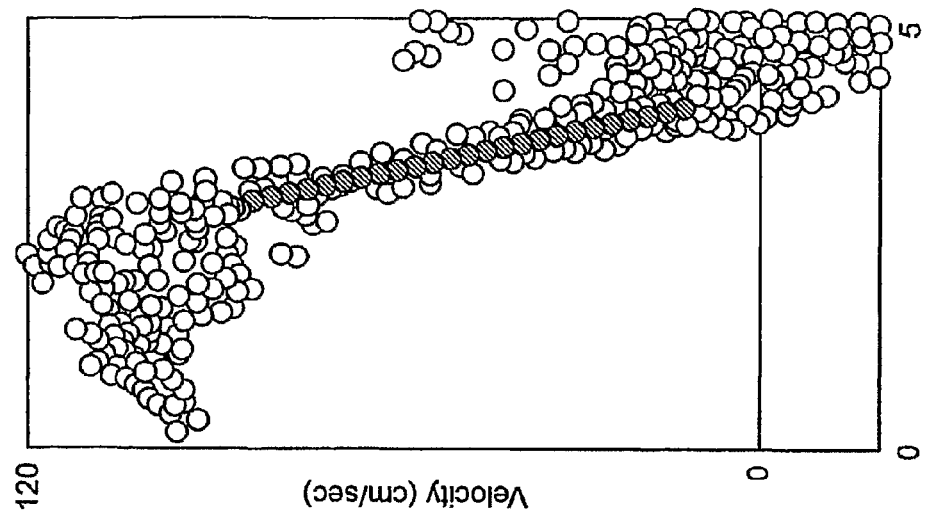
FIGS. 18A-B are graphical views of velocity profile during systole at baseline (FIG. 18A) and at peak hyperemia (FIG. 18B) for the same subject as in FIGS. 16-17. Also shown are the parabola segments that are best-fit to the datapoints near the arterial wall. Shear rate, the slope of the parabola segment near the arterial wall, is increased significantly during hyperemia.
Figure 18A:
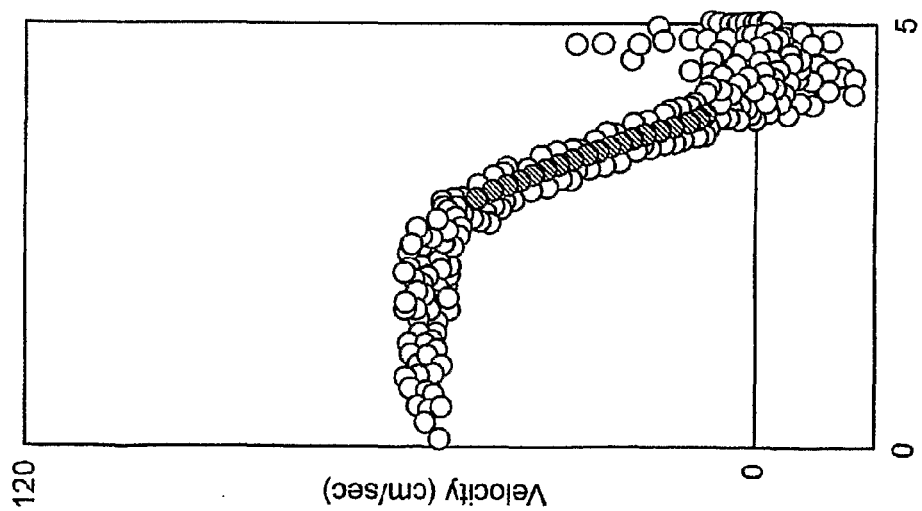

Values are mean ± SD; BP indicates blood pressure; HDL, high density lipoprotein; LDL, low density lipoprotein; P value refers to comparison between groups Total cholesterol and LDL were higher in older than younger men, though the values are within recommended target values in both groups. FIG. 16A shows the magnitude image obtained of a typical femoral arterial cross-section during systole at baseline. Beside the image is radial plot (FIG. 16B) of the magnitude datapoints. The plot also shows a smoothed average of the datapoints and a cross-hatch indicating the point at which the intensity of the smoothed average is half of its maximum (The Full-Width, Half-Maximum method). This was taken as the radius of the artery. FIG. 17A, C shows phase images of peak positive and (FIG. 17A) peak negative (FIG. 17C) flow during the cardiac cycle. Beside each image is a radial plot (FIG. 17B, D) of velocity datapoints. The plots show the best-fit parabola segment to a one-mm wide range near where the velocity profile becomes zero. The slope at zero velocity of the equation for the parabola was taken as the shear rate. FIGS. 18A, B illustrates a radial plot of velocity data during systole for a typical young control subject at baseline (FIG. 18A) and during peak hyperemia (FIG. 18B). Systolic shear rate increased substantially during peak hyperemia.

Measurements from MRI are summarized in Table 5-2.

TABLE 5-2

Magnetic Resonance Imaging Measurements

| Measurement | Young Controls (n = 10) | Older Controls (n = 10) | P |
|---|---|---|---|
| Radius at Baseline, mm | 3.46 ± .37 | 3.52 ± .42 | .36 |
| % Change in Radius (Flow Mediated Dilation) | 1.8 ± 2.0 | 0.7 ± 1.7 | .10 |
| Average Flow at Baseline, ml/min | 284 ± 111 | 270 ± 109 | .39 |
| Average Flow, Peak Hyperemia, ml/min | 1379 ± 342* | 818 ± 301* | .0005 |
| Average Shear Rate at Baseline, sec$^{-1}$ | 134 ± 42 | 123 ± 46 | .28 |
| Average Shear Rate, Peak Hyperemia, sec$^{-1}$ | 587 ± 69* | 309 ± 74* | <.0001 |
| Systolic Shear Rate, Baseline, sec$^{-1}$ | 445 ± 73 | 411 ± 76 | .16 |
| Systolic Shear Rate, Peak Hyperemia, sec$^{-1}$ | 895 ± 123* | 616 ± 129* | <.0001 |

Values are mean ± SD
*p < .0001, Baseline vs. Peak Hyperemia.

Figure 19:
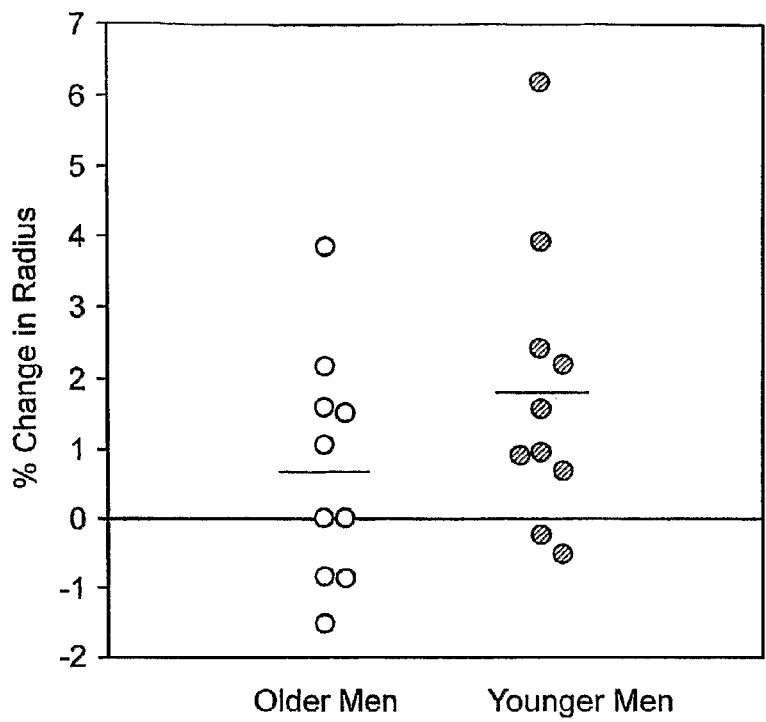
FIG. 19 is a graphical view of flow mediated dilation (% Change in Radius) in older men versus younger men. The mean value was decreased in older men, but the difference did not achieve statistical significance (0.7±1.7% in older men vs. 1.8±2.0% in younger men, p=0.10).
Figure 20:
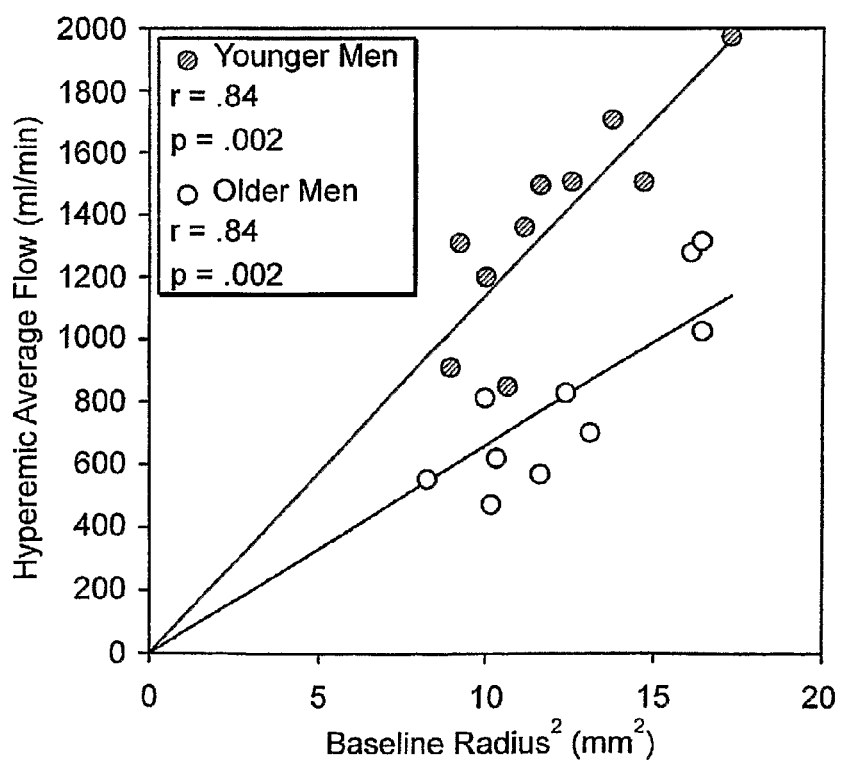
FIG. 20 is a graphical view of hyperemic flow versus radius showing that hyperemic average flow is proportional to radius squared (i.e. proportional to cross-sectional area) for each group, but the slope is decreased in older men.
Figure 21:
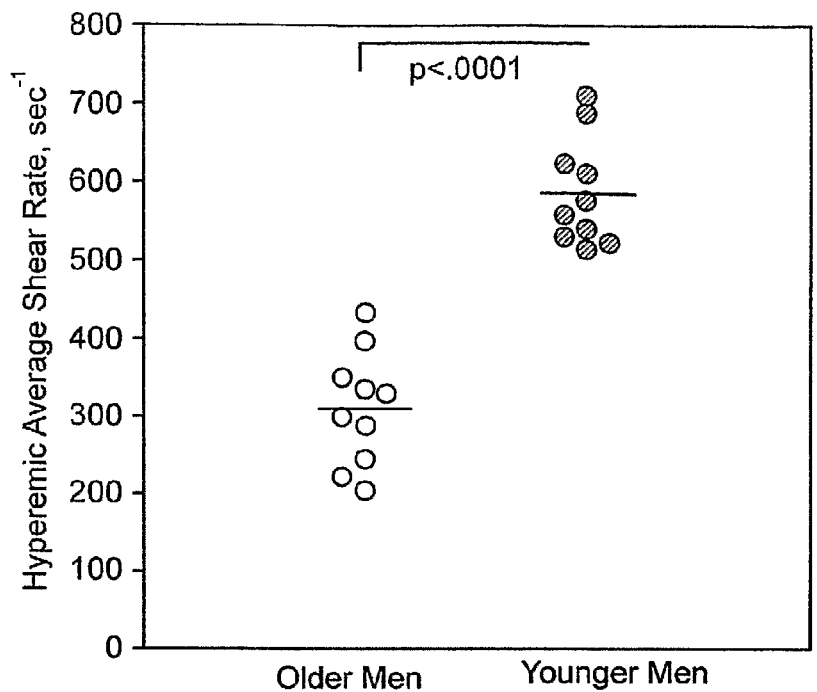
FIG. 21 is a graphical view of average shear rate during peak hyperemia in older men vs. younger men. The two groups are completely separated by this measure.
Figure 22:
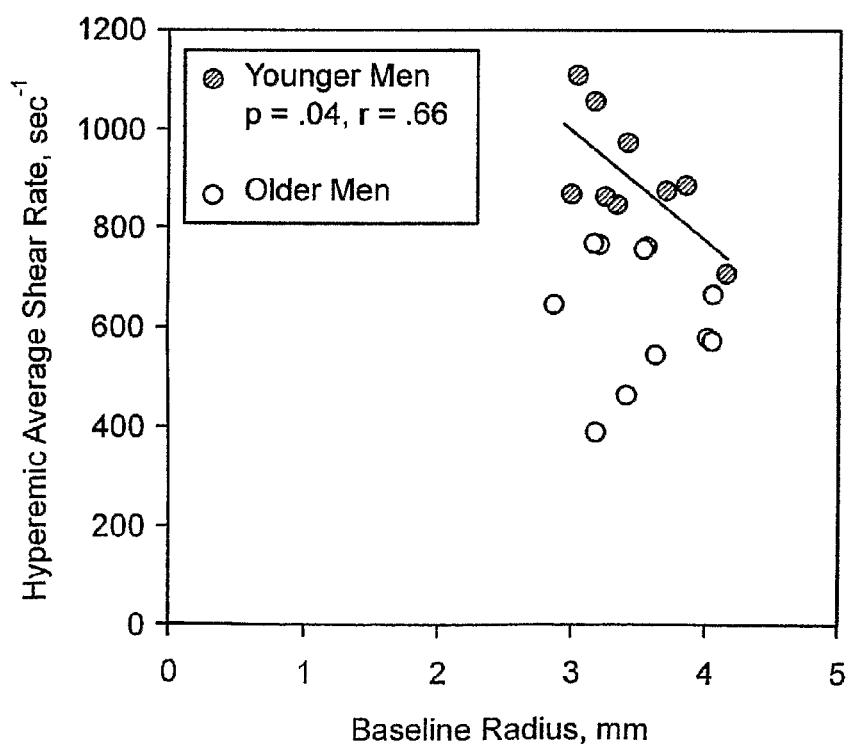
FIG. 22 is a graphical view of systolic shear rate during peak hyperemia as a function of baseline radius in older men (open circles) vs. younger men (closed circles). Hyperemic systolic shear rate is inversely proportional to baseline radius. For any artery size, hyperemic systolic shear rate is decreased in older men.

There was no difference between groups at baseline with regard to radius, average flow, systolic flow, average shear rate, or systolic shear rate. Flow mediated dilation was decreased in older men compared with younger men, but this difference did not achieve statistical significance (FIG. 19). During peak hyperemia, average flow, average shear rate, and systolic shear rate were significantly decreased in older men compared to younger men (Table 5-2). The groups were further distinguished by hyperemic average flow when plotted against radius squared (FIG. 20). Hyperemic flow was proportional to radius squared (i.e., proportional to cross-sectional area) in each group, but the slope was decreased in older men. The measure that distinguished best between the two groups was hyperemic average shear rate (FIG. 21). Indeed, the range of average shear rates during peak hyperemia in older men did not overlap the range in younger men. Hyperemic systolic shear rate was inversely proportional to baseline radius for the younger men but not the older men (FIG. 22). Importantly, hyperemic systolic shear rate was decreased in all older men compared with younger men for any baseline radius.

To address whether differences in hyperemic shear rate were attributable to differences in total cholesterol and LDL, we analyzed a subgroup of 12 subjects—6 older healthy men with the lowest total cholesterol (mean 185) and LDL (mean 103) versus 6 young healthy men with the highest total cholesterol (mean 181, p=0.39 vs. older healthy) and LDL (mean 121, p=0.18 vs. older healthy). The mean total cholesterol and LDL were similar between subgroups, but the subgroups were still completely distinguished by hyperemic shear rate.

The within-subject, repeated measures standard deviations, and the coefficients of variation, respectively, were: Baseline radius, 0.17 mm and 5%; % change in radius (FMD), 1.0% and 87%, baseline average flow, 88 ml/min and 36%; hyperemic average flow, 198 ml/min and 18%; baseline average shear rate, 37 sec$^{-1}$ and 28%; hyperemic average shear rate, 61 sec$^{-1}$ and 14%; baseline systolic shear rate, 18 sec$^{-1}$ and 5%; hyperemic systolic shear rate, 60 sec$^{-1}$ and 10%.

Discussion

In this study, we found that the shear stimulus for flow mediated dilation is markedly reduced in the femoral arteries of healthy older men compared with younger men. Indeed, there was no overlap between younger men and older men with regard to hyperemic average shear rate (FIG. 21). There was also no overlap of hyperemic systolic shear rate for any specific arterial size between groups (FIG. 22). These findings have important implications. First, femoral hyperemic shear rate, the stimulus for FMD, is markedly decreased with increased age and may reflect multiple mechanisms associated with age-related increases in risk. Second, femoral hyperemic shear rate appears to be a more sensitive indicator of abnormal vascular reactivity than FMD.

Aging is associated with impaired peripheral endothelial function in the conduit and resistance arteries. Our analysis indicated that the age-related differences in hyperemic shear rate were not likely to be due to the difference in cholesterol and LDL between the groups.

Direct Measurement of Shear Rate.

Shear rate has been measured directly from the velocity profile in the brachial artery at rest, in the femoral artery at rest, and during hyperemia in the brachial arteries of subjects without risk factors. We previously measured hyperemic shear rate directly in the femoral and brachial arteries of young healthy controls. To our knowledge, this is the first study to measure hyperemic shear rate directly in peripheral arteries of subjects with risk factors such as older age.

Femoral Artery Versus Brachial Artery.

The lower extremity arterial bed is more susceptible to atherosclerosis than that of the upper extremity and has impaired endothelial function. Differences in vascular function between groups with and without risk factors may be magnified in the femoral arteries compared with the brachial arteries. We therefore chose to study the femoral artery and our results show that hyperemic shear rate in the femoral artery appears to be a highly sensitive indicator of abnormal arterial vasodilator function.

Shear Rate and FMD.

Shear stress is the stimulus for flow mediated dilation. However, significant differences in shear stimulus did not translate into significant differences in FMD response in our study. One reason may be the higher variability of FMD measurement than of hyperemic shear rate measurement. The finding of higher variability is supported by another study using phase contrast MRI to assess femoral endothelial function, which reported a lower variability of baseline flow than of FMD. Shear rate was not assessed in that study, but our study found that the variability of average shear rate was similar to that of average flow. We expect that differences in FMD would reach statistical significance between groups if the number of subjects were greater. However, our study suggests that directly measuring hyperemic shear rate requires fewer subjects than FMD would in order to show differences in vascular function between groups. Hyperemic shear rate may even prove useful in evaluating endothelial function in individuals. Another factor that may explain why hyperemic shear rate identified arterial dysfunction better than FMD is the possibility that resistance artery endothelial function (indicated by hyperemic shear rate) is impaired earlier than conduit artery endothelial function (indicated by FMD) in the lower extremity.

Shear Rate and Shear Stress.

Shear stress, the stimulus for FMD, equals shear rate times viscosity. One important factor determining viscosity is hematocrit, which did not differ between older and younger men, and all values were in the normal range. Another factor determining viscosity in a Non-Newtonian fluid like blood is shear rate; i.e. viscosity is decreased at higher shear rates. Based on the ranges of shear rates in our study, the viscosity would not be expected to differ significantly among the subjects.

Example 6

This study compared a ratio of leg-to-arm endothelial function between older diabetics and older nondiabetics using phase contrast magnetic resonance imaging (PCMRI). We assessed endothelial function in by measuring post-ischemic hyperemic shear rate, which is dependent on nitric oxide release from the resistance arterioles.

Methods:

We studied 32 subjects, ages 51-74: 18 nondiabetics with no cardiovascular risk factors (12M/6F), and 14 with type 2 diabetes (12M/2F). ECG-gated PCMRI was performed using a 1.5T scanner. To image the superficial femoral artery, a four-element phased array receiving coil was placed anterior and posterior to the upper thigh, and an inflatable cuff was placed on the lower thigh. For the brachial artery, a 3-inch receiving coil was placed medial to the upper arm and an inflatable cuff was placed on the forearm. PCMRI images were obtained at baseline. The cuff was inflated above the subject's measured systolic blood pressure for 5 minutes, then released. Images using the same fixed cross-sectional axial prescription as at baseline were obtained immediately after cuff release.

A single imaging plane perpendicular to the artery of interest was prescribed. The imaging parameters were: Matrix size 256×128, slice thickness 3 mm, flip angle 25 degrees, bandwidth 31.2 kHz, repetition time (TR) 11.43 msec, echo time (TE) 5.25 msec, 8 views per segment (VPS), first order flow compensation, no phase-wrap, and no magnitude weighting. Settings of 16 signal averages (NEX) were used at baseline, and 2 NEX after cuff release. Field-of-view was 10 by 10 cm for the femoral artery, and 8 by 8 cm for the brachial artery. During peak hyperemia, 10 VPS was used if necessary to keep the scanning time at 35 seconds or less. Maximum encoded velocity (VENC) was 60-70 cm/sec during baseline, and 120-150 cm/sec during peak hyperemia. Resulting temporal resolution was 90-180 msec.

A user-independent algorithm was employed to measure arterial radius and shear rate from the phase images. A radial plot of the velocity of each pixel versus its distance from the optimal center of the cross-section was created. The velocity pixels near the lumen wall were fit by least-squares method to a parabola. Shear rate was calculated as the slope of the velocity profile at the lumen-wall interface during systole. Radius was defined as where the best-fit parabola equals zero.

Results:

There was no difference between diabetics and nondiabetics at baseline with regard to age (61±7 vs. 58±6 years, p=0.12), femoral radius (3.77±0.34 vs. 3.66±0.50 mm, p=0.43), femoral shear rate (397±96 vs. 424±86 sec$^{-1}$, p.29), brachial radius (2.45±0.34 vs. 2.39±0.33 mm, p=0.33), brachial shear rate (402+145 vs. 358±110 sec$^{-1}$, p=0.18), or ratio of femoral radius to brachial radius (1.56±0.20 vs. 1.57±0.22, p=0.37). The ratio of baseline femoral-to-brachial shear rate tended to be lower in diabetics but did not reach statistical significance (1.06±0.32 vs. 1.23+0.27, p=0.07). During hyperemia, the ratio of femoral-to-brachial shear rate was significantly reduced in diabetics compared with nondiabetics (0.59+0.16 vs. 0.78+0.27, p=0.01).

Conclusions:

Endothelial function is more impaired in the lower extremity than the upper extremity in type 2 diabetics. This suggests that there are regional differences in endothelial dysfunction that may explain why atherosclerosis development is usually more severe in the leg than arm vessels. Measuring hyperemic shear rate using MRI is useful in explaining mechanisms underlying atherogenesis.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A non-transitory applications program for execution on a computer, the non-transitory applications program for processing magnetic resonance image data acquired using a phase-contrast MRI scan technique to assess vascular reactivity during an arterial occlusion, said non-transitory application program comprises instructions, criteria and code segments for:
   (a) finding a center of the arterial cross-section being imaged using one of an MRI magnitude image or an MRI phase image of the phase contrast MRI scan;
   (b) fitting a parabolic curve using selected data of the MRI phase image;
   (c) using an equation of the fitted parabolic curve to measure shear rate; and
   (d) calculating a radius of the arterial cross-section using one of the MRI magnitude image or the MRI phase image.

2. The non-transitory applications program of claim 1, further comprising instructions, criteria and code segments for:
   (e) determining flow from the phase image and the determined center of the arterial cross-section.

3. The non-transitory applications program of claim 1, wherein said calculating a radius of the arterial cross-section includes instructions, criteria and code segments for
   (1) calculating the distance from the center of the arterial cross-section to where intensity drops to half of a maximum intensity and setting the radius equal to the calculated distance, when the center of the arterial cross-section is found using the MRI magnitude image; and (2) calculating the radius using the equation of the fitted parabolic curve, where the velocity is zero at an interface of the lumen and wall of the artery, when the center of the arterial cross-section is found using the MRI phase image.

4. The non-transitory applications program of claim 1, wherein the selected data used for fitting the parabolic curve is a radial segment defined by an inner and outer point, the outer point being at a radius corresponding to where velocity drops is determined to be less than a percentage of a maximum value and where the inner point is a predetermined distance from the outer point.

5. The non-transitory applications program of claim 1, wherein said equation of the fitted parabolic curve to measure shear rate further includes instructions, criteria and code segments for calculating a slope at where the velocity would equal zero.

6. The non-transitory applications program of claim 1, wherein the magnetic resonance image data also is being processed to assess vascular reactivity after an arterial occlusion.

7. The method of claim 1, further comprising the step(s) of:
dividing the acquired images into N sectors, N being an integer;
wherein said calculating wall shear stress includes calculating shear stress for each of the N sectors; and
averaging the measured shear stress of the N sectors to yield an average shear stress.

8. A computer system for processing magnetic resonance image data to assess vascular reactivity during an arterial occlusion, said system comprising:
a computer including a microprocessor;
a non-transitory applications program for execution on the microprocessor; and
wherein said non-transitory application program comprises instructions, criteria and code segments for:
(a) finding a center of the arterial cross-section being imaged using one of an MRI magnitude image or an MRI phase image;
(b) fitting a parabolic curve using selected data of the MRI phase image;
(c) using an equation of the fitted parabolic curve to measure shear rate; and
(d) calculating a radius of the arterial cross-section using one of the MRI magnitude image or the MRI phase image.

9. The computer system of claim 8, wherein the non-transitory applications program further includes instructions, criteria and code segments for:
(e) determining flow from the phase image and the determined center of the arterial cross-section.

10. The computer system of claim 8, wherein said calculating a radius of the arterial cross-section includes instructions, criteria and code segments for
(1) calculating the distance from the center of the arterial cross-section to where intensity drops to half of a maximum intensity and setting the radius equal to the calculated distance, when the center of the arterial cross-section is found using the MRI magnitude image; and
(2) calculating the radius using the equation of the fitted parabolic curve, where the velocity is zero at an interface of the lumen and wall of the artery, when the center of the arterial cross-section is found using the MRI phase image.

11. The computer system of claim 8, wherein the selected data used for fitting the parabolic curve is a radial segment defined by an inner and outer point, the outer point being at a radius corresponding to where velocity drops is determined to be less than a percentage of a maximum value and where the inner point is a predetermined distance from the outer point.

12. The computer system of claim 8, wherein said equation of the fitted parabolic curve to measure shear rate further includes instructions, criteria and code segments for calculating a slope at where the velocity would equal zero.

13. A method for assessing vascular reactivity during an arterial occlusion, comprising:
constricting an artery for a period of time, such that the artery is fully occluded;
using a magnetic resonance image scanner to obtain images of an artery from which a pixel array can be acquired, said images being obtained prior to occlusion (at baseline), as well as one or more times during and after occlusion;
using a first pixel array to determine a center of the arterial cross-section;
fitting a parabolic curve to velocity data taken from a second pixel array of the phase image;
using an equation of the parabolic curve to measure shear rate; and
calculating a radius of the arterial cross section using the equation of the parabolic curve.

14. The method of claim 13 further comprising determining shear rate by calculating a slope of the parabolic curve at a point where a velocity is zero.

15. The method of claim 13 further comprising the radius of the arterial cross section being a point at which a velocity of the parabolic curve is zero.

16. The method of claim 13 further comprising determining a flow for the artery by summing velocity pixels having a distance from a center point of the parabolic curve that is less than the radius.

17. A method for assessing vascular reactivity during an arterial occlusion, comprising:
constricting an artery for a period of time, such that the artery is fully occluded;
using a magnetic resonance image (MRI) scanner to obtain images of an artery from which a pixel array can be acquired, said images being obtained prior to occlusion (at baseline), as well as one or more times during and after occlusion;
using a first pixel array to determine a center of the arterial cross-section;
dividing image data from the images obtained from the (MRI) scanner into N sectors surrounding the center of the arterial cross section;
determining an outer radius of the velocity profile for each of the sectors and determining corresponding datapoints;
fitting a parabolic curve to the datapoints;
calculating the slope of the parabolic curve at a lumen-wall interface to determine shear rate; and
calculating a radius of the artery by determining a distance from a center of the parabolic curve to a point where the parabolic curve crosses zero velocity.

18. The method of claim 17 further comprising choosing an image of the artery with the greatest peak velocity for analysis.

19. The method of claim 17 further comprising fitting the parabolic curve to the datapoints using a least-squares method.

20. The method of claim 17 further comprising N=12 sectors.

* * * * *